United States Patent
Denton et al.

(10) Patent No.: US 9,134,272 B2
(45) Date of Patent: Sep. 15, 2015

(54) SENSITIVE ION DETECTION DEVICE AND METHOD FOR ANALYSIS OF COMPOUNDS AS VAPORS IN GASES

(71) Applicant: THE ARIZONA BOARD OF REGENTS ON BEHALF OF THE UNIVERSITY OF ARIZONA, Tucson, AZ (US)

(72) Inventors: M. Bonner Denton, Tucson, AZ (US); Roger P. Sperline, Tucson, AZ (US)

(73) Assignee: The Arizona Board of Regents on behalf of the University of Arizona, Phoenix, AZ (US)

( * ) Notice: Subject to any disclaimer, the term of this patent is extended or adjusted under 35 U.S.C. 154(b) by 0 days.

(21) Appl. No.: 14/046,447

(22) Filed: Oct. 4, 2013

(65) Prior Publication Data
US 2014/0151545 A1 Jun. 5, 2014

Related U.S. Application Data

(63) Continuation of application No. 12/741,811, filed as application No. PCT/US2008/082589 on Nov. 6, 2008, now Pat. No. 8,653,449.

(60) Provisional application No. 61/002,121, filed on Nov. 6, 2007.

(51) Int. Cl.
*H01J 49/00* (2006.01)
*G01N 27/62* (2006.01)
(Continued)

(52) U.S. Cl.
CPC .............. *G01N 27/622* (2013.01); *H01J 49/02* (2013.01); *H01J 49/10* (2013.01)

(58) Field of Classification Search
CPC .......................................... H01J 49/00–49/406

USPC ........................................................ 250/283
See application file for complete search history.

(56) References Cited

U.S. PATENT DOCUMENTS 3,639,757 A * 2/1972 Caroll et al. .................. 250/282
4,121,458 A 10/1978 Fort
(Continued)

FOREIGN PATENT DOCUMENTS

JP 2005524196 A 8/2005
JP 2005276837 A 10/2005
(Continued)

OTHER PUBLICATIONS

Supplementary European Search Report issued on Feb. 2, 2013 in the corresponding EP application 08871397.9.
(Continued)

*Primary Examiner* — Phillip A Johnston
(74) *Attorney, Agent, or Firm* — Lathrop & Gage LLP

(57) ABSTRACT

An ion mobility spectrometer (IMS) for the detection of trace gaseous molecular compounds dissolved or suspended in a carrier gas, particularly in ambient air, without preconcentration or the trapping of analyte particles. The IMS of the invention comprises an ionization volume of greater than 5 cm$^3$ and preferably greater than 100 cm$^3$. The larger size ionizers of this invention enable analysis of trace (<1 ppb) of sample compounds in the gas phase. To facilitate efficient ion motion through the large volume ionization and reaction regions of the IMS, an electric field gradient can be provided in the ionization region or in both the ionization and reaction regions. The systems can be implemented with radioactive ionization sources, corona discharge ion sources or ions can be formed by photoionization. In specific embodiments, particularly when the sample gas is ambient air, the sample gas is heater prior to entry into the instrument, the instrument is run at temperatures above ambient, and the instrument can be heated by contact with heated sample gas exiting the instrument.

19 Claims, 15 Drawing Sheets

(51) Int. Cl.
    *H01J 49/10*     (2006.01)
    *H01J 49/02*     (2006.01)

(56) References Cited

U.S. PATENT DOCUMENTS

| | | | |
|---|---|---|---|
| 4,777,463 A | 10/1988 | Eiceman et al. | |
| 5,153,432 A | 10/1992 | Devant et al. | |
| 5,175,431 A | 12/1992 | Eisele et al. | |
| 5,200,614 A | 4/1993 | Jenkins | |
| 5,218,203 A | 6/1993 | Eisele et al. | |
| 5,310,681 A | 5/1994 | Rounbehler et al. | |
| 5,563,410 A | 10/1996 | Mullock | |
| 5,585,575 A | 12/1996 | Corrigan et al. | |
| 6,630,662 B1 | 10/2003 | Loboda | |
| 6,791,078 B2 | 9/2004 | Giles et al. | |
| 6,906,319 B2 | 6/2005 | Hoyes | |
| 6,992,283 B2 | 1/2006 | Bateman et al. | |
| 7,081,618 B2 | 7/2006 | Laprade | |
| 7,095,019 B1 | 8/2006 | Sheehan et al. | |
| 7,227,132 B2* | 6/2007 | Guervremont et al. | 250/287 |
| 7,538,320 B2* | 5/2009 | Sperline | 250/286 |
| 7,569,812 B1 | 8/2009 | Sheehan et al. | |
| 7,608,818 B2* | 10/2009 | Miller et al. | 250/288 |
| 8,653,449 B2 | 2/2014 | Denton et al. | |
| 2004/0238755 A1 | 12/2004 | Lee et al. | |
| 2007/0007448 A1 | 1/2007 | Wang | |
| 2007/0187591 A1 | 8/2007 | Bromberg et al. | |
| 2008/0179515 A1 | 7/2008 | Sperline | |
| 2011/0036977 A1 | 2/2011 | Denton et al. | |

FOREIGN PATENT DOCUMENTS

| | | |
|---|---|---|
| WO | WO0122049 | 3/2001 |
| WO | WO2007095203 | 8/2007 |

OTHER PUBLICATIONS

Cross, J. A. (1985) "An Analysis of The Current In a Point-To-Plane Corona Discharge and The Effect of a Back-Ionizing Layer on The Plane." *J. Phys. D: Appl. Phys.* 18(12):2463-2471.

Hill, H.H. et al. (1990) "Ion Mobility Spectrometry," *Anal. Chem.* 62(23):1201A-1209A.

International Search Report and Written Opinion, Corresponding to International Application No. PCT/US2008/082589, Mailed Sep. 11, 2009.

Jaworek, A.; Krupa, A. (1995) "Electrical Characteristics of a Corona Discharge Reactor of Multipoint-To-Plane Geometry." Czechoslovak J. Phys. 45(12):1035-1047.

Knight, A.K. (Dec. 2006) "Advanced detection technology for ion mobility and mass spectrometry," Ph.D. Dissertation, Department of Chemistry, University of Arizona.

Siegel, M.W. (1984) "Atmospheric Pressure Ionization," in T.W. Carr (Ed.), Plasma Chromatography, Plenum Press, New York, Chapter 3, pp. 95-113.

Madani et al. (1998) "Current Density Distribution Measurement of Negative Point-To-Plane Corona Discharge." *IEEE Transactions on Instrumentation and Measurement* 47(4):907-913.

Mu et al. (2003) "Effects of interfacial interaction potential on the sublimation rates of TNT films on a silica surface examined by QCM and AFM techniques." *Surface Science* 530(1-2):L293-L296.

Siems et al. (Dec. 1994) "Measuring the resolving power of ion mobility spectrometers," *Anal. Chem.* 66(23):4195-4201.

Wu et al. (1998) "Electrospray Ionization High-Resolution Ion Mobility Spectrometry-Mass Spectrometry," *Anal. Chem.* 70:4929-4938.

Alexandre A. Shvartsburg, Richard D. Smith, Ashley Wilks, Andrew Koehl, David Ruiz-Alonso, and Billy Boyle "Ultrafast Differential Ion Mobility Spectrometry at Extreme Electric Fields in Multichannel Microchips," Anal. Chem. (Jul. 2009), 81, 6489-6495.

Alexandre A. Shvartsburg, Keqi Tang, Richard D. Smith, Martin Holden, Martyn Rush, Andrew Thompson, and Danielle Toutoungi "Ultrafast Differential Ion Mobility Spectrometry at Extreme Electric Fields Coupled to Mass Spectrometry," Anal. Chem. (Aug. 2009), 81, 8048-8053.

Alexandre A. Shvartsburg, Richard D. Smith "Accelerated High-Resolution Differential Ion Mobility Separations Using Hydrogen," Anal. Chem. (Nov. 2011), 83,9159-9166.

E. Nazarov, T.A. Postlethwaite and Q. Shi "Planar Differential Mobility Spectrometry as a Powerful Tool for Gas Phase Ion Separation and Detection" (2013) Spectroscopy Solutions, 2013 (Draper report No. P-6024) downloaded Nov. 26, 2014 from http://www.spectroscopy-solutions.org/Information/Archive/Featured-Articles/2220-/Planar-Differential-Mobility-Spectrometry-as-a-Powerful-Tool-for-Gas-Phase-Ion-Separation-and-Detection.

Klassen et al (1997) Reactant Ion Chemistry for Detection of TNT, RDX, and PETN Using an Ion Mobility Spectrometer, Sandia Report SAND97-2165 UC 741 Sandia national Laboratories.

Niu, W. et al. (May 2011) Mobility Spectrometry Studies on Hydrazine and Ammonia Detection, NASA Technical Reports, Document ID: 20110011195, 41st International Conference on Environmental (ICES); Jul. 17-21, 2011; Portland, OR; United States American Inst. of Aeronautics and Astronautics; Reston, VA, United States.

Stach J. and Baumbach, J.I. (2002), Ion Mobility Spectrometry—Basic Elements and Applications, Int J. Ion Mobility Spect. 5 (1):1-21.

Stano, M. et al. (Aug. 31, 2008) Ion Mobility Spectrometry Study of Negative Corona Discharge in Oxygen/Nitrogen Mixtures Chem. Listy 102:s1414-s1417, Association of Czech Chemical Societies 2nd Central European Symposium on Plasma Chemistry Aug. 31-Sep. 4, 2008 Brno, Czech Republic.

Vautz, W. et al. (2004) Sensitive Ion Mobility Spectrometry of Humid Ambient Air Using 10.6 EV UV-IMS, Int. J. Ion Mobility Spect. 7 (1):1-8.

* cited by examiner

SENSITIVE ION DETECTION DEVICE AND METHOD FOR ANALYSIS OF COMPOUNDS AS VAPORS IN GASES

CROSS-REFERENCE TO RELATED APPLICATIONS

This application is a continuation of U.S. application Ser. No. 12/741,811, filed May 6, 2010, which is the U.S. National Stage of International Application No. PCT/US2008/082589, filed Nov. 6, 2008, which claims the benefit of U.S. provisional application 61/002,121 filed Nov. 6, 2007, each of which is incorporated in its entirety by reference herein.

STATEMENT REGARDING FEDERALLY SPONSORED RESEARCH OR DEVELOPMENT

This invention was made with government support under grant no. DE-AC04-94-AL85000 awarded by the Department of Energy. The government has certain rights in the invention.

BACKGROUND OF THE INVENTION

The present invention is related in general to the field of detecting materials and specifically to an ion detection device with a gaseous sample inlet and ionizer that provide for increased sensitivity in the detection of traces of materials in the vapor phase. The device of the present invention has achieved superior sensitivity to vapor phase analytes without either the use of condensation or concentration of the vapors as liquids or solids and without the collection of analyte material as droplets or particles. Used in conjunction with condensation or concentration of analyte materials, even greater sensitivity could be achieved.

The rapid identification of explosives, explosive residues, chemical agents, airborne toxins, and other volatile organic compounds has undergone a revolution in recent years by the progress made in the field of ion mobility instruments. Despite the transformation that has occurred in ion mobility spectrometry, the full potential of the technique has not yet been realized, particularly in the analysis of gases. This is partially due to the low numbers of ions generated in the small ionizers employed in conventional ion mobility spectrometers. As will be appreciated by one of ordinary skill in the art, existing devices are limited in detecting traces of materials by the low number of ions generated by the materials in a ionization chamber because the existing devices require a certain number of ions (above a threshold) to be present in order to detect the materials from which the ions originated.

FIG. 1 shows a typical ion mobility spectrometer (IMS) that includes an ionization region 1 and a reaction chamber 10 in which a gas 7 enters and is ionized, an ion drift chamber 15 coupled in series with the reaction chamber 10 through an ion injection shutter 12, and a collector plate 16 disposed inside the drift chamber 15, opposite the injection shutter 12. In operation, a carrier gas transports gases or vapor from a material to be analyzed into an ionization region 1 containing an ionization source 2. A repeller electrode 4 (also called a pusher electrode), which may be in the form of a plate or a screen, is provided in the ionization region to direct ions toward the drift chamber. Most of the resulting ions (primary ions) are from the carrier gas molecules ("reactive or reactant ions"), which move to the reaction chamber (10) where multiple collisions occur between ionized species and the analyte molecules. These collisions transfer ion charges to the analyte molecules forming secondary ions. It is also known in the art to employ a reagent gas which is introduced into the reaction region so that secondary ions are predominantly formed from the reagent interacting with primary ions. In this case, sample is also introduced into the reaction region and charge is transferred from the primary and secondary ions to the analyte (tertiary ions.) All ions move, predominantly, by "electrophoresis" in the electric field inside the spectrometer. The electric field, formed by conventional techniques, moves ions from the reaction chamber 10 to the drift chamber 15 and ultimately to reach the collector plate 16. Typically, a drift gas is introduced into the drift chamber and exits through gas exit 9. The combined portions of the apparatus, outside the ionizer, where ions move by electrophoresis are called, generically, the "drift tube." Hill, H. H. et al. (1990) "Ion Mobility Spectrometry," Anal. Chem. 62(23):1201A-1209A and Eiceman, G. A., Karpas, Z. (2005) *Ion Mobility Spectrometry*, (CRC Press) provide reviews of ion mobility spectrometry, including instrumentation.

U.S. Pat. No. 4,777,363 reports an atmospheric ion mobility spectrometer for detection of trace substances in ambient air. In this spectrometer the air acts as the sample, carrier and drift gases. In a "uniflow design," ambient air is introduced through an inlet at the collector end of the drift tube and a gas exit with a pump is provided at the opposite end of the instrument beyond the ion source. A repeller plate is provided at the end of the instrument having the drift gas exit. Ions formed at the ion source and secondary ions formed on reaction move into the drift chamber as ion pulses formed at an ion shutter. Ions in the drift chamber move in a direction opposite the direction of flow of the air drift gas. Ions are detected at the collector plate. The reference describes the use of a Ni-63 (radioactive source) ion source. The reference describes a "typical Ni-63 source" as a cylinder of Ni (1 to 2 cm in diameter and 1-2 cm long with surface area of 3-5 $cm^2$) with Ni-63 plated on the inner surface. It is stated that a "major limitation in the linear response range has been attributed to a limited availability of ions from the ion source." The reference describes a higher activity ion source as "a nickel slug approximately 3 to 5 cm in diameter with a plurality of holes for Ni-63 plating." This ion source is said to provide "a much higher surface area and activity rate without requiring an increase in the size of the ion source." A photoionization source is also described. The instrument is said to be pneumatically sealed with a pump on the repeller end.

U.S. Pat. No. 5,218,203 reports a high pressure interface device for introducing sample ions to a drift tube of a ion mobility measurement means. The patent describes an "isolated" ionization source which is illustrated in FIG. 1 of the patent to be at the ion source gas (B1) inlet. It is stated that "it is important that the ionization of the ion source gas occurs in an isolated region where no sample gas is present." The sample gas ions formed are described as introduced into a second reaction region where they react with a sample gas (B2) to form sample ions. The device configuration used is described as minimizing or eliminating introduction of unwanted components into the drift tube. The patent discusses the presence of an electric field E to direct the ion source gas ions through the flow path of the sample gas.

SUMMARY OF THE INVENTION

The present invention provides instrumentation and methods for the detection, by ion mobility spectrometry (IMS), of trace gaseous molecular compounds dissolved or suspended in a carrier gas, particularly in ambient air, without preconcentration or the trapping of analyte particles.

Contrary to the conventional practice in IMS of using small volume (<1 cm$^3$) ionizers, the present invention uses significantly larger volume ionizers of at least 5 cm$^3$. In preferred embodiments, the ionizers employed herein have volume greater than 25 cm$^3$, greater than 50 cm3 and more preferably have volume greater than 100 cm$^3$. The upper limit of the ionization volume is not particularly limited, however, a likely upper limit for reasonable applications is about 100 L. In specific embodiments, the ionization volume is greater than 0.5 L. In other specific embodiments, the ionization volume is between 0.5 and 2 L. In additional specific embodiments, the ionization volume is between 0.5 and 1 L. The larger size ionizers of this invention enable analysis of trace (<1 ppb) sample compounds in the gas phase.

To facilitate efficient ion motion through the ionization and reaction regions, systems of this invention are preferably provided with an electric field gradient in the ionization region or in both the ionization and reaction regions. The electric field gradient provided is parallel to that formed in the drift region. The EFG needs to be present in both the ionization and reaction regions, but can be of different values between the two, and the gradients need not necessarily be linear.

In a specific embodiment, ambient air is the sample gas in an IMS of this invention. In another embodiment, particularly when the sample gas is ambient air, the sample gas is heater prior to entry into the instrument, particularly to a temperature between 50 C and 120 C. In another embodiment, the instrument is run at temperatures above ambient, particularly at temperatures between 50 C and 120 C. In another embodiment, the instrument is heated by contact with heated sample gas exiting the instrument In a specific embodiment, the ion mobility spectrometer is operated at atmospheric pressure.

Separately, the present invention can be combined with other sample introduction methods for the pre-separation of analyte molecules to provide for the quantitation of analyte mixtures.

Separately, the gas analysis technique of the present invention can be combined with other sample introduction techniques for the preconcentration of analyte materials to provide sensitivity beyond that of either technique alone.

In a specific embodiment for the detection of low vapor-pressure compounds in air, the invention provides an IMS having an ionizer volume of 50 cm$^3$ or more and preferably having an ionizer volume of 500 cm$^3$ or more. The instrument of this embodiment is particularly useful for the detection of low vapor-pressure compounds such as TNT at its saturation concentration of 1 ppb in air.

In the present invention, an ionization chamber and reaction chamber are provided that allow the efficient introduction and ionization of sufficient gas to contain a detectable quantity of analyte at a concentration as small as what would be equivalent to 5 ppt or below of analyte of TNT in air.

Contrary to conventional practice that requires humidity control in the gases used in IMS analyses, the instruments and methods of the present invention do not require humidity control of gases. Particularly, when ambient air is be analyzed, there is no need for humidity control of the ambient air.

Contrary to conventional practice that employs the addition of reagent compounds to enhance sensitivity of the analyses of certain sample compounds, the instruments and methods of the present invention do not require the use of reagent compounds, Furthermore, to avoid entrainment of ions in air flow away from the ion shutter it is desirable that the cross sectional area of the ionizer and reaction region should be large enough such that local linear flow velocities in a direction perpendicular to the direction of sample ion electrophoresis is not a significant fraction (e.g., less than 20% or preferably less than 10%) of the velocity of the sample ion electrophoresis. This limit should be low enough to not significantly reduce instrumental sensitivity. In the case of counter-flow of the carrier gas to the direction of sample ion electrophoresis, the local linear flow rates should not exceed the linear velocity of sample ion electrophoresis. Preferably, it should not exceed 25% of the sample ion electrophoresis velocity.

According to another aspect of the present invention, various possible means for creation of reactive ions within the ionization chamber are provided.

In specific embodiments, the invention provides an ion mobility spectrometer comprising an ionization region having an ion source, a reaction region, a drift region and an ion detector wherein the ionization volume of the ionization source is greater than 5 cm$^3$. In more specific embodiments, the ionization volume of the ionization source is greater than 100 cm$^3$ or it si between 0.5 L and 2 L, inclusive.

In a specific embodiment, the ion detector is a collector, such as a Faraday plate. In other embodiments, the ion detector is a mass spectrometer. In additional embodiments, the ion detector is a quadropole mass spectrometer with an electron multiplier detector.

In specific embodiments, the invention provides an ion mobility spectrometer comprising an ionization region having an ion source, a reaction region, a drift region and a collector for detection of ions wherein the ionization volume of the ionization source is greater than 5 cm$^3$ and where in an electric field gradient is provided in the ionization region or in both the ionization region and the reaction region to facilitate movement of ions from the ionization region and reaction region to the ion shutter and the drift region.

The ion mobility spectrometers of this invention can comprise one or more radioactive ionization sources. The ion mobility spectrometers of this invention can comprise one or more corona discharge ion sources. The ion mobility spectrometers of this invention can comprise one or more multi-point corona discharges.

The ion mobility spectrometers of this invention can further comprise a heater or cooler for adjusting the temperature of the sample gas entering the spectrometer.

In a specific embodiment, the invention provides an ion mobility spectrometer wherein the ionization volume of the ionization source is greater than 0.5 L and wherein an electric field gradient in the ionization region or in both the ionization and reaction regions.

In the ion mobility spectrometers of this invention of claim 8, the electric field gradient in the ionization region can be provided by a plurality of ring electrodes.

The invention further provides a method for detecting low levels of analyte in a sample gas by ion mobility spectroscopy employing an IMS spectrometer of this invention. In such methods, a sample gas containing low levels of analyte is introduced into the ionization volume of the IMS wherein substantially the entire volume of the ionization region is subjected to ionization such that analyte ions are formed in an amount sufficient for detection in the IMS.

In specific embodiments of the methods herein, the sample gas is ambient air. In specific embodiments of the methods herein, the analyte is a low vapor pressure analyte. In specific embodiments of the methods herein, the analyte is TNT or another explosive compound.

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

Figure 1:
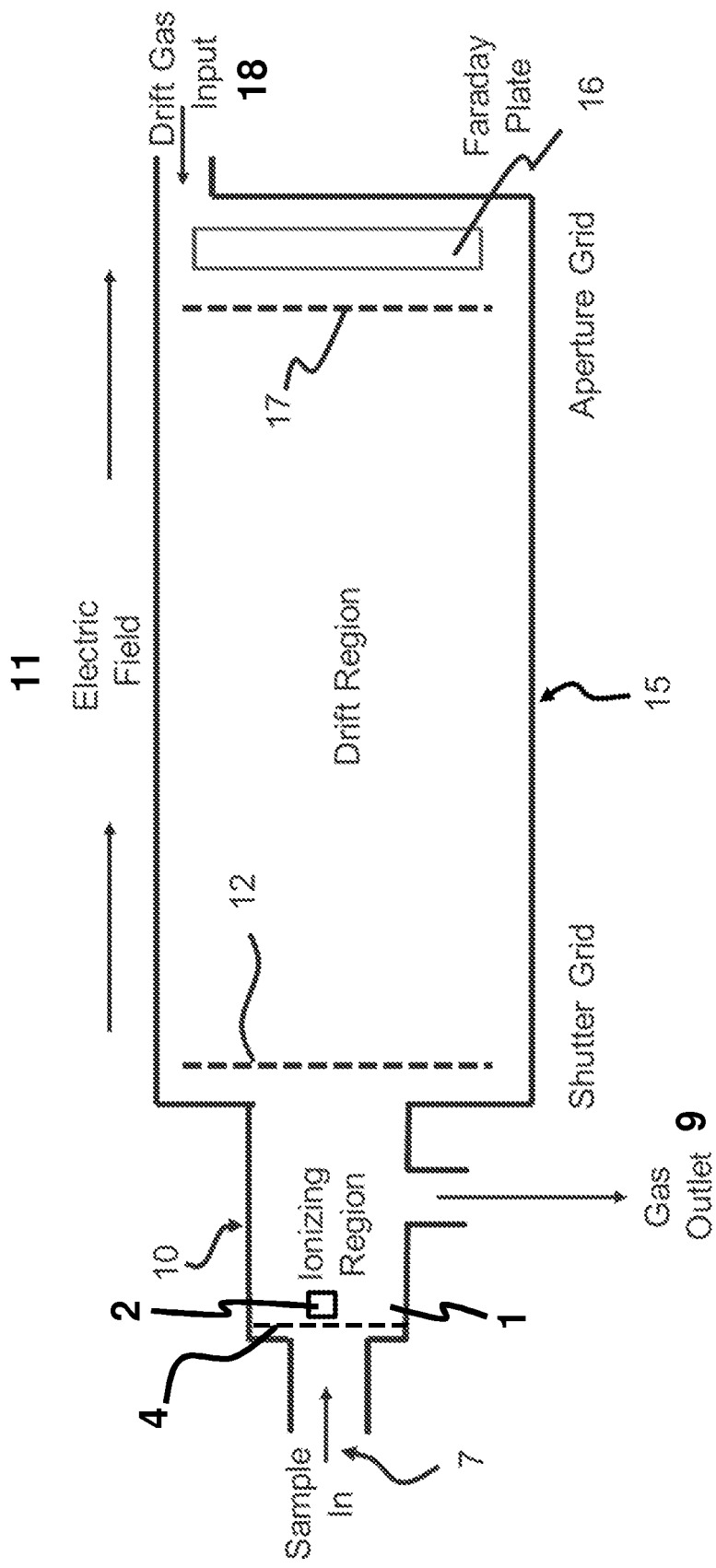
FIG. 1 is a schematic diagram of a prior art ion mobility spectrometer.

The term "ion mobility spectrometer" is used broadly herein to refer to an instrument that detects and identifies an analyte by differential migration of gas phase ions of the analyte through an appropriate monotonic electric field. IMS detection is based on ion mobility. IMS systems, as shown in FIG. 1, typically comprise an ionization region, a reaction region, an ion shutter, a drift region containing a drift gas and an ion detector (collector, which can be a Faraday plate). A repeller and aperture grid are optionally provided. IMS systems further comprise one or more gas inlets and one or more gas outlets for introduction and exit of any carrier, sample or reagent gases to the ionization or reaction region or for introduction and/or exit of drift gas. A fan or pump can optionally be provided for gas circulation in the system. An electric field gradient is provided in the drift region, typically employing ring electrodes as is known in the art. Primary, secondary and optionally tertiary ions are formed in the ionization and reactor region (some of which are analyte ions). A repeller at the ionization end of the instrument can be provided to direct ions toward the reaction and drift regions. An aperture grid can be provided as a guard for the collector plate to prevent precharging of the collector. This grid can also help maintain the uniformity of the electric field responsible for the motion of the ions. Various ion sources can be employed in IMS, including alpha- and beta-emitting radioactive sources (e.g., Ni-63 and Am-241 sources), corona discharge sources, photoionization sources, and the like. IMS often employs an ion collector, such as a Faraday plate for ion detection. Other ion detectors can be employed as is known in the art. For example, IMS spectrometers can be linked to a mass spectrometer, such as a quadropole mass spectrometer, for ion detection and identification. See, for example, Wu, C., Siems, W. F., Asbury, G. R., Hill, H. H. "Electrospray Ionization High-Resolution Ion Mobility Spectrometry-Mass Spectrometry," (1998) Anal. Chem. 70:4929-4938.

Various gas flow configurations can be employed in IMS as is known in the art. For example, carrier gas or sample gas (e.g., ambient air) can flow through the ionization chamber either in the same direction as the analyte ions travel under electrophoresis toward the ion detector ("co-flow"), alternatively carrier gas flow can be in the opposite direction to the direction of electrophoresis ("counter-flow"), or carrier gas flow can be transverse to the direction of electrophoresis ("cross-flow"). Reagent gas, if used, is typically introduced separately from carrier or sample gas. Carrier gas may be the sample gas (e.g., carrying one or more analytes) or carrier gas may be different from and introduced at a location different from sample gas.

Ion entry into the drift region is gated employing an ion shutter as is known in the art. Gated ions move in the electric field gradient of the drift region toward the collector where they are detected. IMS can be operated in positive or negative ion mode as is known in the art. Positive ions are detected in positive ion mode or negative ions are detected in negative ion mode. The ion current formed at the collector can be amplified as is known in the art. The results of ion collection of multiple ion packets can be averaged to improve the final signal-to-noise ratio also as is known in the art. Data collected is analyzed using any known expedient, for example, a personal computer with attached data acquisition hardware and software can be employed. Additional detail so IMS can be found in Hill, H. H. et al. (1990) "Ion Mobility Spectrometry," Anal. Chem. 62(23):1201A-1209A and Eiceman, G. A., Karpas, Z. (2005) *Ion Mobility Spectrometry*, (CRC Press) each of which is incorporated by reference herein in its entirety.

The volume of an ionizer or ion source is used herein to refer to the volume of gas that can be ionized by a given ionizer or ion source. With respect to a radioactive ion source, such as a Ni-63 source, which comprises one or more surfaces carrying the radioactive isotope, the ionizer volume depends upon the number, size, shape and relative position of these surfaces and the penetration length in air of the particles emitted by the radioisotope For example, the beta-particles emitted by Ni-63 have a penetration length in air of about 3 mm so for an ion source of length of about 5 mm the ionizer volume is about 0.14 $cm^3$ The improved IMS of this invention is further described herein with respect to the drawings where the same number in different figures represents the same or related device elements. The drawings are schematic and not necessarily drawn to scale.

Figure 2A:
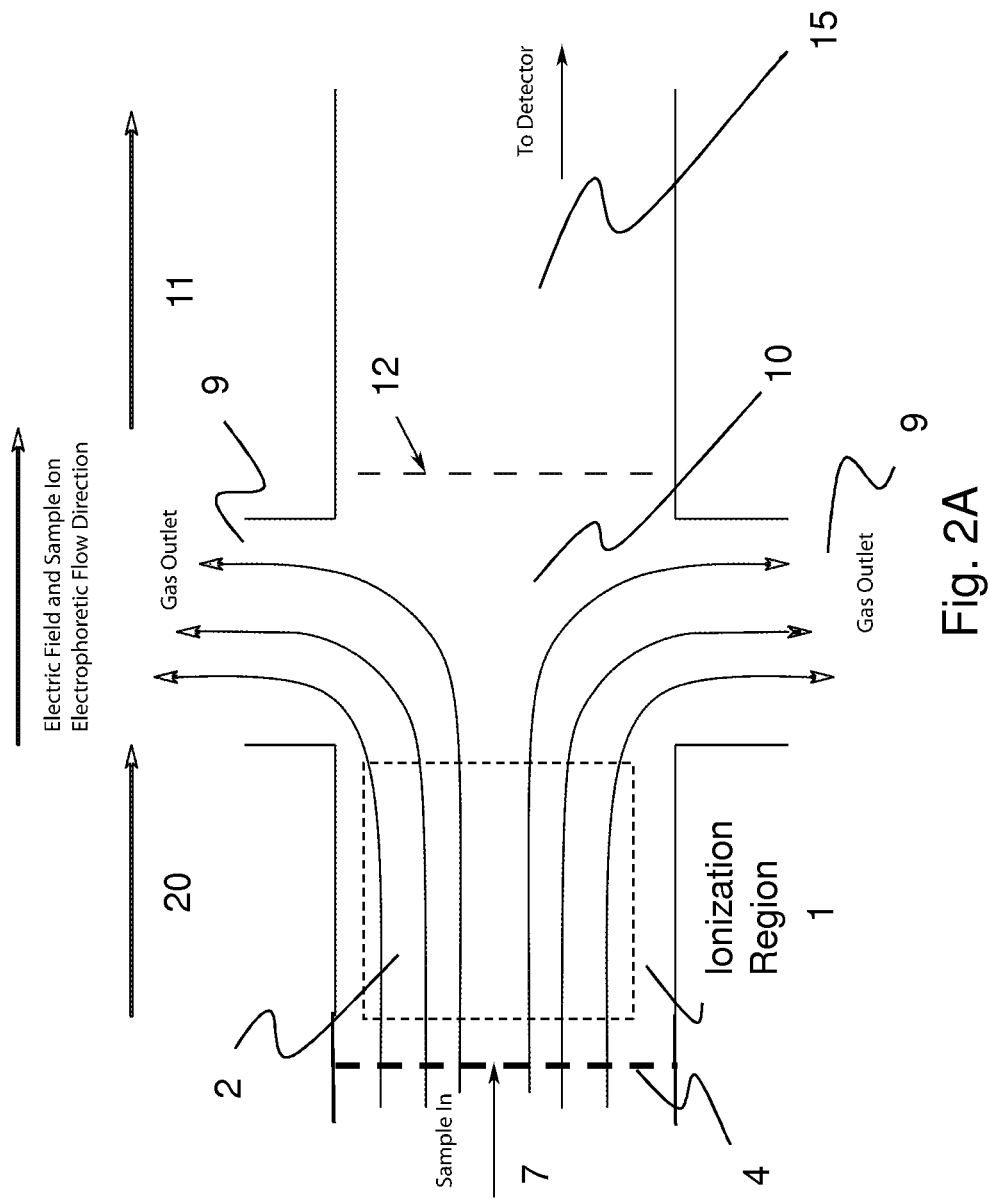
FIG. 2A is a schematic diagram, focusing on the ionization region, of an exemplary system of the present invention where sample-containing gas passes through the ionizer in the same direction as the direction of electrophoresis of analyte ions. The preferred location of the radioactive ionization source is shown. This ionization region can also be used for photoionization with the deletion of the radioactive source by providing a transparent wall in the ionization region.

FIG. 2A illustrates an exemplary ionization region 1 of the present invention in relation to the reaction region 10, sample inlet 7, gas outlets 9 and drift region 15. The ionization source 2 is illustrated in the ionization region. In this embodiment, sample (carrier) gas (e.g., ambient air) flows into the ionization region in the same direction as the direction of ion electrophoretic flow.

Figure 2B:
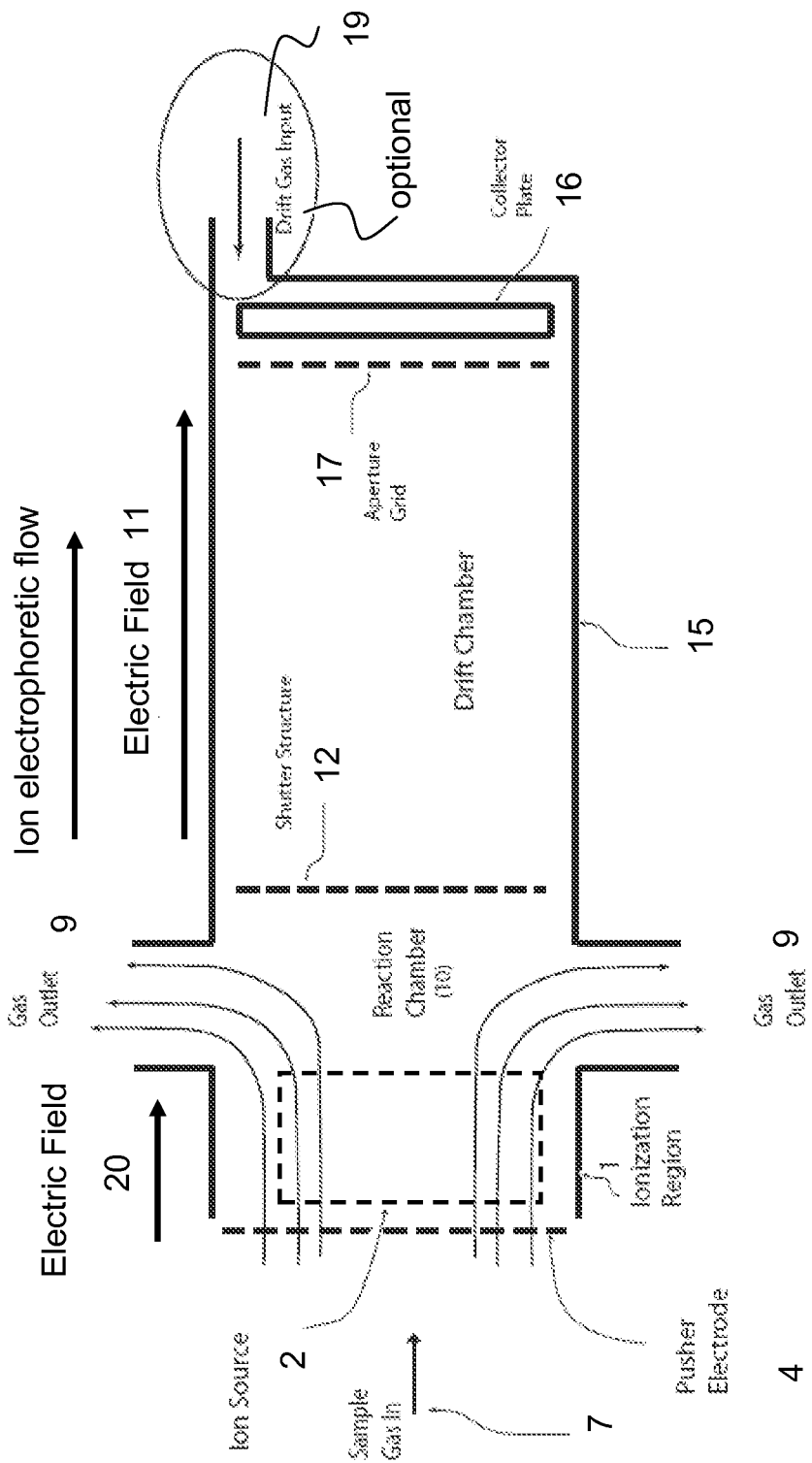
FIG. 2B is a schematic drawing of an ionization mobility spectrometer having the sample introduction, ionization and reaction regions of FIG. 2A. The system is illustrated with placement of a radioactive ion source. As noted for FIG. 2A, and as will be discussed herein below, the ionization region can be adapted for use of ion sources other than radioactive ion sources, such as corona discharge sources and for photoionization.

FIG. 2B illustrates an IMS system having the sample gas flow, ionization and reaction regions of FIG. 2A. The figure indicates the position of a repeller (pusher electrode 4) which directs ions formed in the ionizer region to the reaction region and on to the drift region. The reaction region is separated from the drift region by an ion shutter. Sample gas enters at inlet 7 and exits at gas outlets 9. The figure shows a drift gas input 19 which is optional. Drift gas may be flowed through the drift region to exit at the gas outlets. In this embodiment, the drift region (drift chamber) is sealed for entrance of exogenous gases. For example, it may be desired to conduct the ion mobility determination employing a gas other than air, e.g., nitrogen. In a specific embodiment of this invention for the analysis of analytes in ambient air, there is no specific drift gas input and the drift chamber is not sealed to entry by ambient air which functions as the drift gas. It has been noted in the instruments of this invention that it is not necessary to dry ambient air before it is introduced into the system. It is noted that instruments can optionally be provided with filters for removing undesired components from sample or drift gas. As is know in the art, the drift region is provided with an electric filed gradient which causes ions in the drift tube to move toward the collector.

As noted above in order to generate larger numbers of ions needed to detect trace analytes, the ionization regions of the IMS of this invention have larger ionization volumes than conventional IMS systems. In specific embodiment, ionization volumes are greater than 50 $cm^3$ or greater than 100 $cm^3$. In more specific embodiments, the ionization volume is between 0.1 and 1.0 liters (100 $cm^3$ and 1000 $cm^3$) or between 0.5 and 1.0 liters. In these embodiments for trace gas analysis, it is preferred that substantially all (95% or more) of the sample gas volume introduced into the IMS is subjected to ionization. Preferably the ionization volume is substantially matched (95% or greater) to the volume of the ionization region of the IMS.

In embodiments of this invention, the ionization region is provided with an electric field gradient 20 to facilitate ion electrophoresis to the reaction region and the drift region. This embodiment is particularly useful if the ionization volume (along the axis of the IMS) is more than 25% of the diameter (cylinder) [or height or width for a rectangle] of the ionization volume. For example, a plurality of ring electrodes can be provided to facilitate ion electrophoresis to the reaction region and the drift region. The word "ring" is used to describe any electrode structure that will produce a controlled field gradient.

Figure 2C:
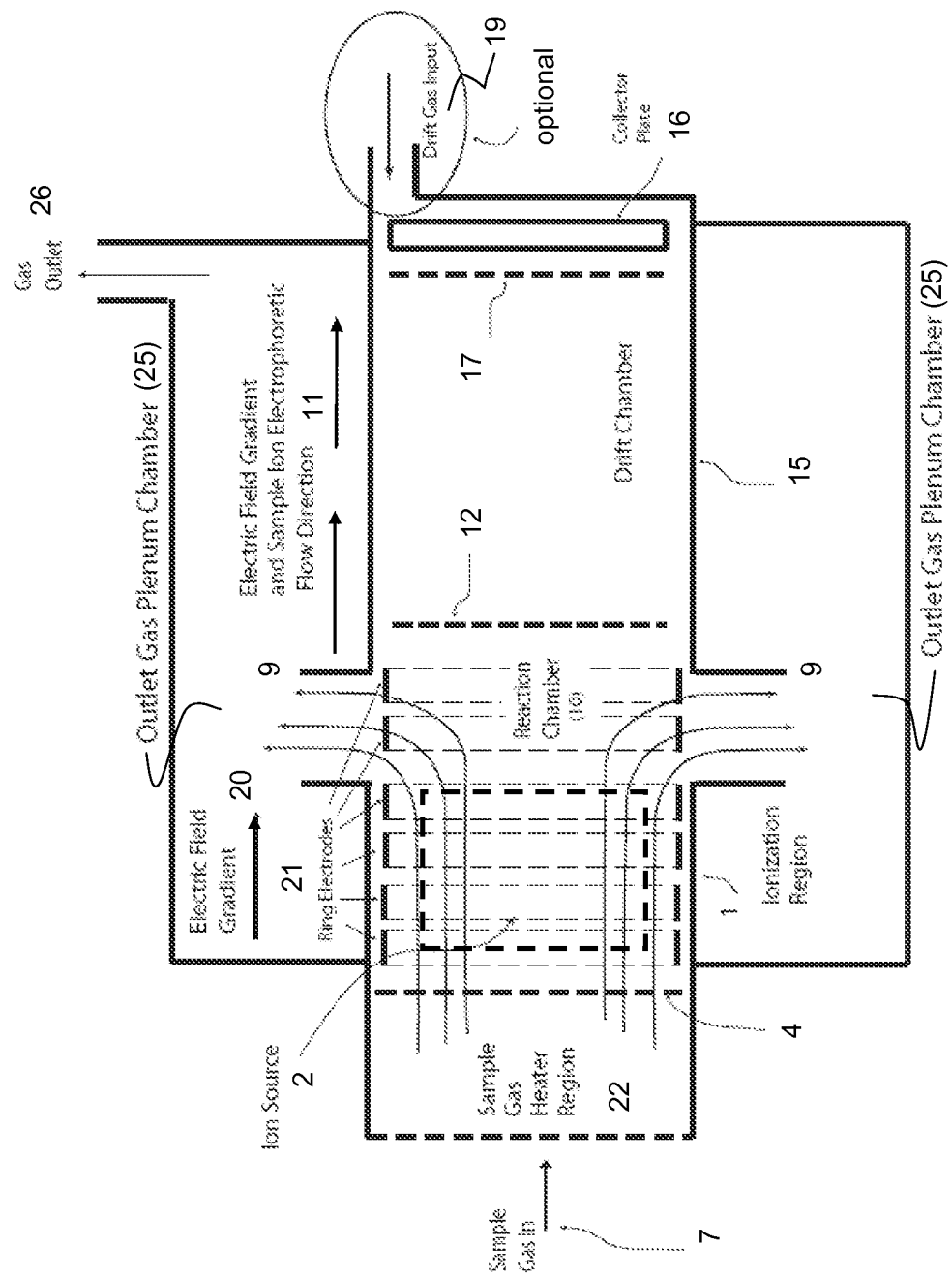
FIG. 2C is a schematic drawing of an exemplary embodiment of an ionization mobility spectrometer of this invention having the sample introduction, ionization and reaction regions of FIG. 2A. The system is illustrated with placement of a radioactive ion source. The drawing illustrates the incorporation of an electric field gradient in the ionization region to facilitate drift of ions through the ionization and reaction region. An ionization drift region is formed analogously to the drift region (15), for example, employing a series of ring electrodes. The word "ring" is used to describe any electrode structure that will produce a controlled field gradient.

FIG. 2C illustrates several specific embodiments of the invention comprising the ionization region of FIG. 2A. In a first embodiment, an electric filed gradient is provided in the ionization region as discussed above, by providing a plurality of ring electrodes. The electrodes may be evenly spaced along the length of the ionization region. The ring electrodes can extend through the reaction region as well. The electrical connection of these ring electrodes is shown in more detail in FIG. 2D. This figure illustrates preferred relative positioning of the ion source, repeller, ring electrodes and shutter. It will be apparent to one of ordinary skill in the art, that various electrode configuration can be employed to provide the desired electric field gradient. The word "ring" is used to describe any electrode structure that will produce a controlled field gradient.

Also illustrated in FIG. 2C is an embodiment in which the sample gas is heated prior to entry into the system in a heater region 22 and wherein sample gas exiting the instrument enters an outlet gas plenum which surrounds the instrument. Heater sample gas is thus employed to heat the entire instrument. The instrument can be run at ambient temperatures or at temperatures above ambient. In a specific embodiment, the instrument is run at temperatures above 50 C. In a specific embodiment, the instrument is run at temperatures between 50 C and 120 C. In a specific embodiment, the instrument is run at a temperature of 100 C. In an alternative, embodiment, an IMS of this invention can be run at temperatures below ambient, by providing a cooler or cooling agent. For example, sample gas can be cooled to a desired temperature prior to introduction into the IMS system and the cooled sample gas exiting the system can be employed to cool the system.

Figure 2D:
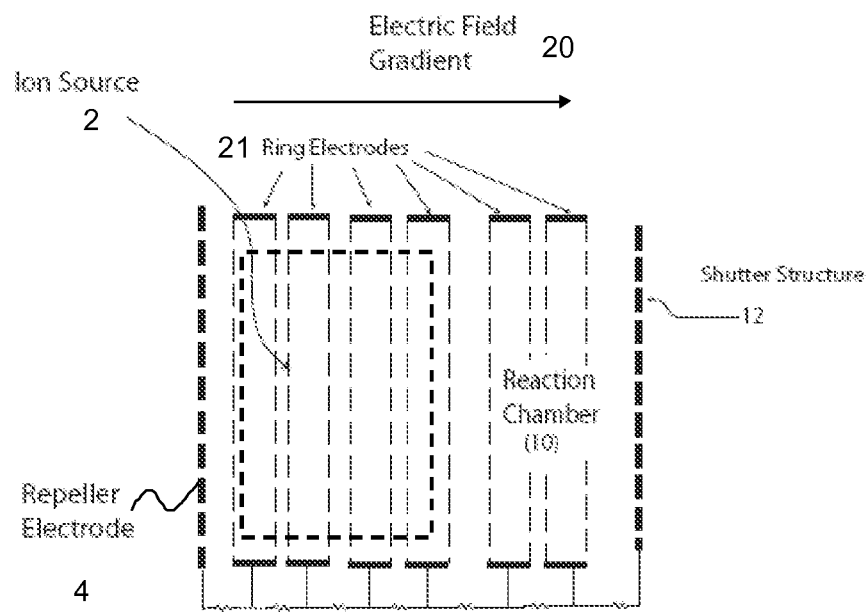
FIG. 2D is a schematic drawing illustrating in more detail the features of the electric field gradient of FIG. 2C. A plurality of ring electrodes is provided between a repeller and the ion shutter.
Figure 3:
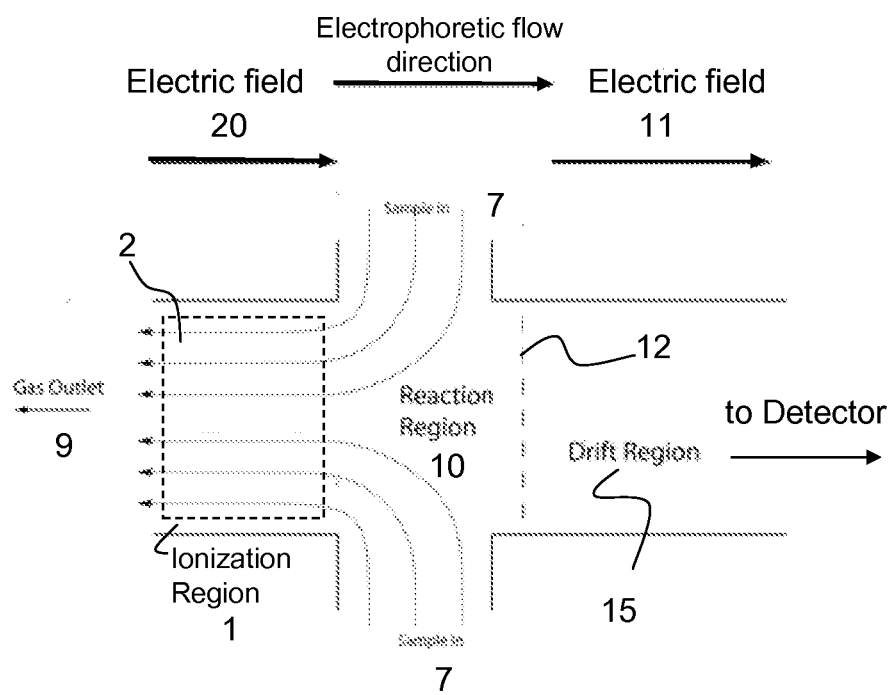
FIG. 3 is a schematic diagram, focusing on the ionization region, of another exemplary embodiment of the instrument of the present invention where sample-containing gas passes through the ionizer in the opposite direction to the direction of electrophoresis of analyte ions. The drawing illustrates use of a radioactive ionization source. The ionization region illustrated can be adapted for photoionization and the use of ion sources other than radioactive ion sources, such as corona discharge sources. The features of the illustrated sample introduction, ionization and reaction region can be incorporated into IMS systems as illustrated in FIGS. 2B, 2C and 2D.

FIG. 3 illustrates another exemplary ionization region 1 of the present invention in relation to the reaction region 10, sample inlet 7, gas outlets 9 and drift region 15. The ionization source 2 is illustrated in the ionization region. In this embodiment, sample (carrier) gas (e.g., ambient air) flows into the ionization region in the direction opposite to the direction of ion electrophoretic flow. The configuration of FIG. 3 can be implemented in any of the devices illustrated in FIGS. 2B-2D.

Figure 4:
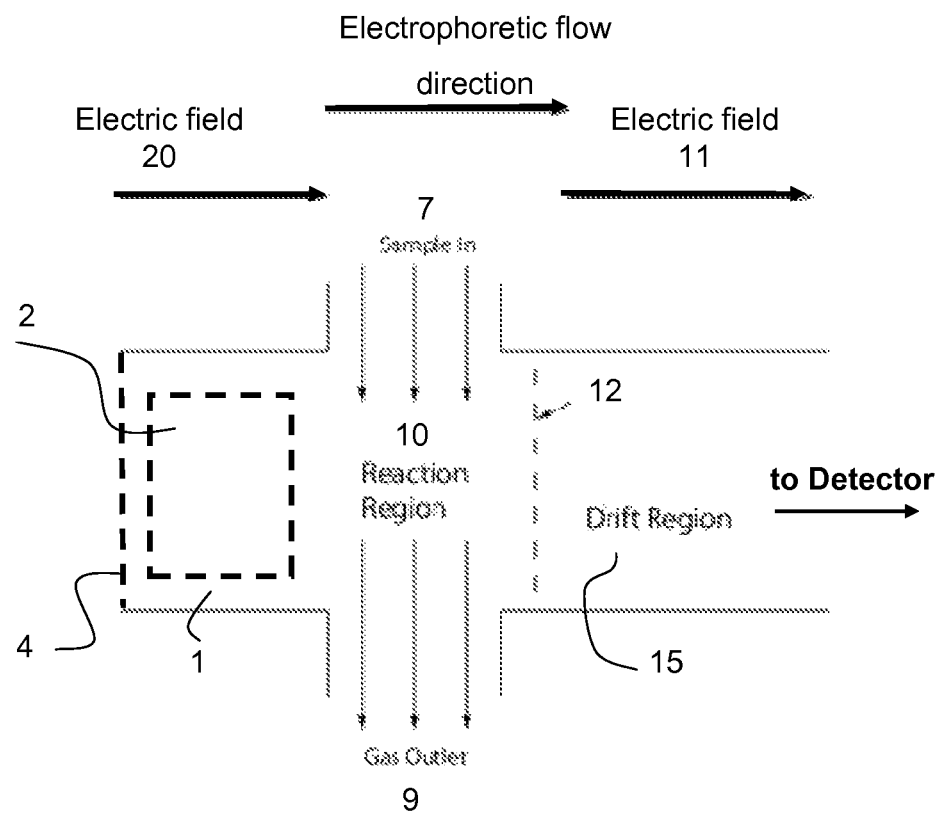
FIG. 4 is a schematic diagram, focusing on the ionization region, of another exemplary embodiment of the instrument of the present invention where sample-containing gas passes through the ionizer in a direction transverse to the direction of electrophoresis of analyte ions. The drawing illustrates use of a radioactive ionization source. The ionization region illustrated can be adapted for photoionization and the use of ion sources other than radioactive ion sources, such as corona discharge sources. The features of the illustrated sample introduction, ionization and reaction region can be incorporated into IMS systems as illustrated in FIGS. 2B, 2C and 2D.

FIG. 4 illustrates illustrate another exemplary ionization region 1 of the present invention in relation to the reaction region 10, sample inlet 7, gas outlets 9 and drift region 15. The ionization source 2 is illustrated in the ionization region. In this embodiment, sample (carrier) gas (e.g., ambient air) flows into the ionization region in a direction perpendicular to that of ion electrophoretic flow. The configurations of FIG. 3 or FIG. 4 can be implemented in any of the devices illustrated in FIGS. 2B-2D. It will be appreciated that the gas flow rates must be adjusted so the applied electric field still carries the ions to the ion shutter.

FIGS. 5-12 illustrate various exemplary radioactive ionization source configurations that are useful in the IMS of this invention. These configurations are useful particularly to achieve high efficiency ionization in larger ionization volumes. These configurations can be implemented with any appropriate radioisotope useful in ion sources and particularly for Ni-63 and Am-241 sources. In each configuration it is intended that the entire volume within the illustrated cylinder is subjected to ionization. The diameters of various ion source elements, and the spacing between such elements is adjusted based on the penetration length of particles emitted by the radioactive source employed.

Figure 5:
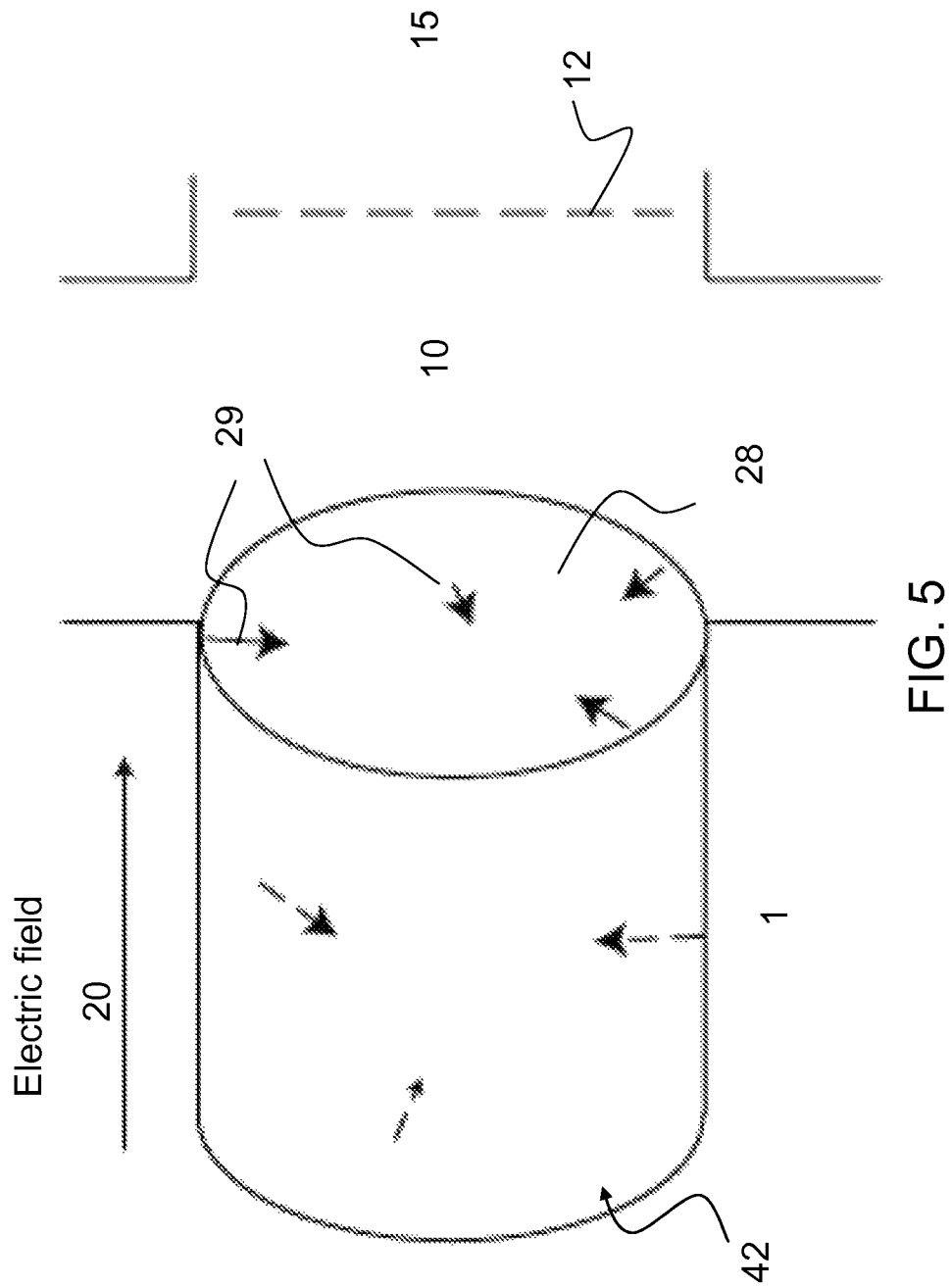
FIGS. 5-12 are schematic drawings illustrating exemplary embodiments of radioactive ion source configurations for use in the ionization regions and IMS of this invention. Each of the illustrated ion source configuration can be employed in the instruments of any of FIG. 2B-2D, 3 or 4.

FIG. 5 illustrates an embodiment in which the inner surface 28 of an ion source element 42 (in the form of a tube) is coated or otherwise provided with an appropriate radioactive isotope. The tube 42 may be formed by the wall of the ionization region or be a separate element within the ionization region. This figure illustrates the relative position of the ion source in the ionization region with respect to the reaction region 10, the ion shutter and drift region. The arrows indicate the direction of emission of alpha or beta particles from the radioactive material on the inner surface 28. Preferably the diameter of tube 42 is equal to or less than 2× the penetration length of the emitted particles.

Figure 6:
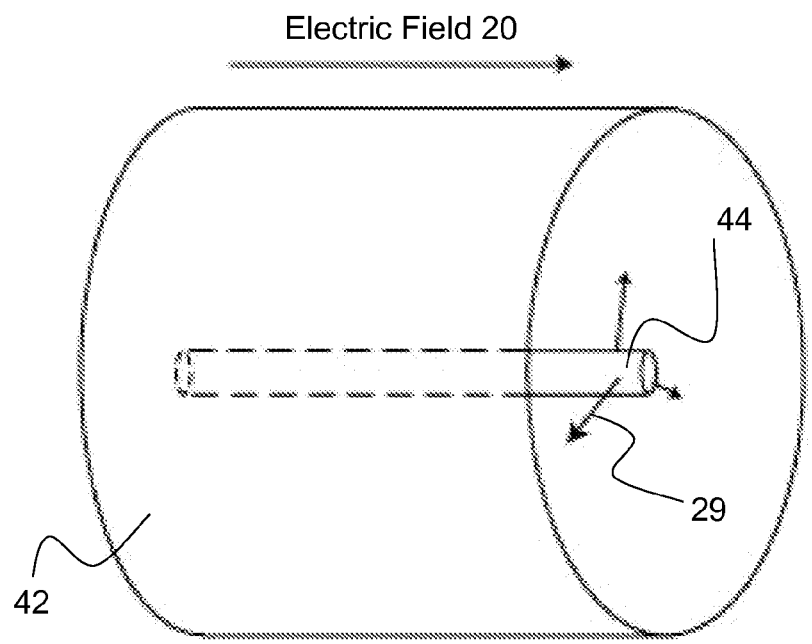

FIG. 6 illustrates another ion source embodiment in which the ion source element is a single cylindrical bar 44 positioned in the ionization region. The cylindrical bar is illustrated as centered within a tube 42 which may be the walls of the ionization region. The bar emits particles from its surface as illustrated by the arrows (29). Dependent upon the diameter of the bar, the diameter of the outer tube is preferably at most about 2× the penetration length of the emitted particles.

Figure 7:
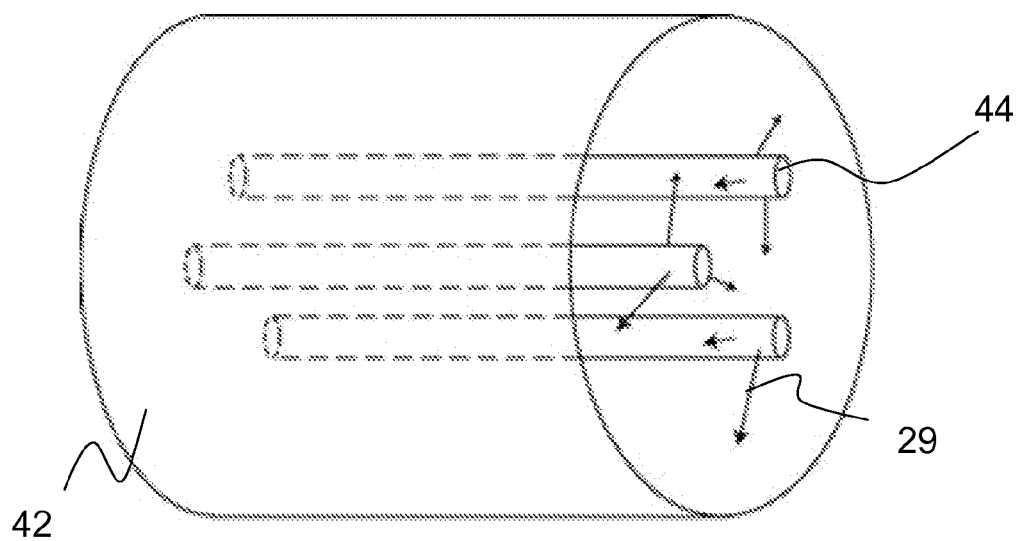
Figure 8:
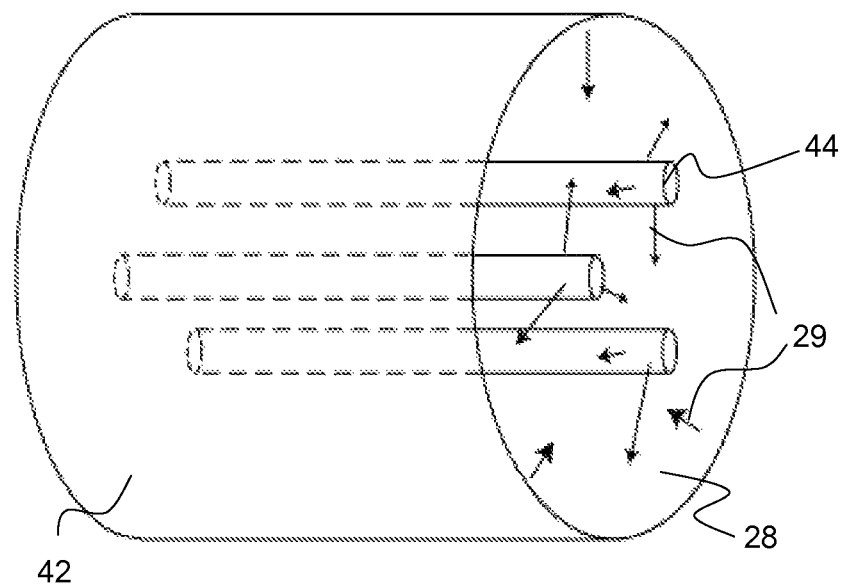

FIG. 7 illustrates another embodiment in which the ion source comprises a plurality of elements (cylindrical bars 44 which emit particles from their surfaces). FIG. 8 illustrates yet another ionization source embodiment comprising an outer tube 42 and a plurality of cylindrical elements 44 positioned within the tube each of which emit particles. In this case, the inside surface of the outer tube (28) is also provided with a radioactive isotope and emits particles. The number of cylindrical emitting bars 44 and their relative placement in these embodiments can also be adjusted to ensure that the entire volume of the ionization region is subjected to emitted particle. The number of bars is not particularly limited, except that gas flow through the ionization region should not be particularly limited. In specific embodiments, 1-10 such bars may be provides. In each case, preferably the outer tube 42 diameter is adjusted based on the penetration length of the radioisotope(s) employed, such that the entire volume of the ionization region is subjected to ionization. The ionization region and the ion source elements are illustrated as cylindrical in shape. These elements are not particularly limited in shape and their size is adjusted to obtain the ionization volume desired and such that substantially all of the ionization region volume is exposed to emitted particles. Different radioisotopes may be provided on different surfaces.

Figure 9:
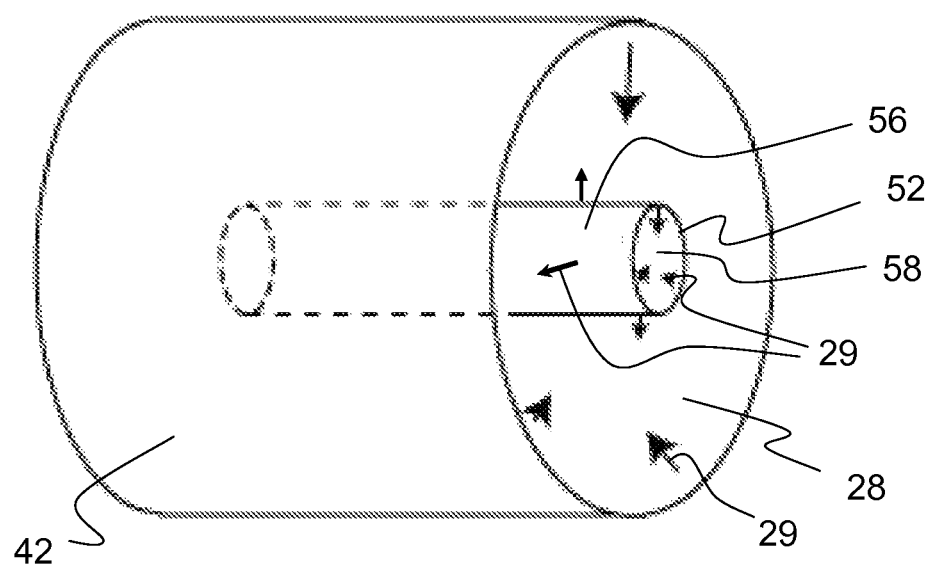
Figure 10:
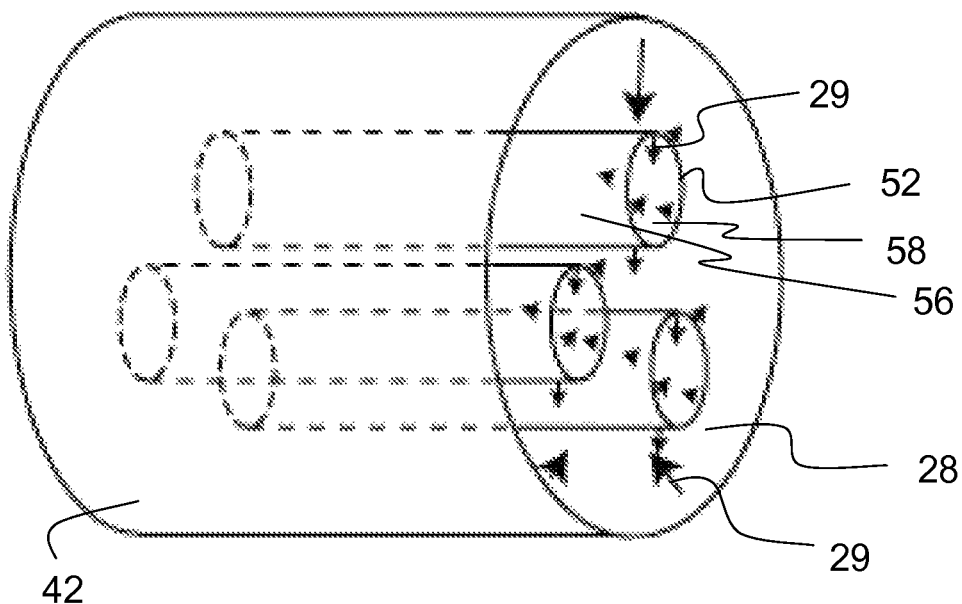

FIGS. 9 and 10 illustrate additional exemplary ion source configurations in which the ion source elements are one or more tubes 52 within an outer tube 42. In FIG. 9, the inner surface (28) of the outer tube and the inner (58) and outer surfaces (56) of the inner tube are provided with radioisotope, so that particles are emitted (see arrows 29) from these surfaces. The outer tube 42 diameter and the diameter of the inner tube 52 are adjusted to maximize the volume to which emitted particles extend. FIG. 10 illustrates a related embodiment in which a plurality of inner tubes 52 is provided within a larger diameter outer tube 42. Again the inner surface of the outer tube (28) and the inner (58) and outer (56) surfaces of the inner tubes (52) are provided with radioisotope(s) and emit particles. The outer tube diameter and the number, relative placement and diameters of the inner tubes 52 are adjusted to maximize the volume within the ionization region to which emitted particles extend. The ionization region and the ion source elements are illustrated as cylindrical in shape. These elements are however not particularly limited in shape and their size is adjusted to the ionization volume desired and such that substantially all of the ionization region volume is exposed to emitted particles. Different radioisotopes may be provided on different surfaces.

Figure 11:
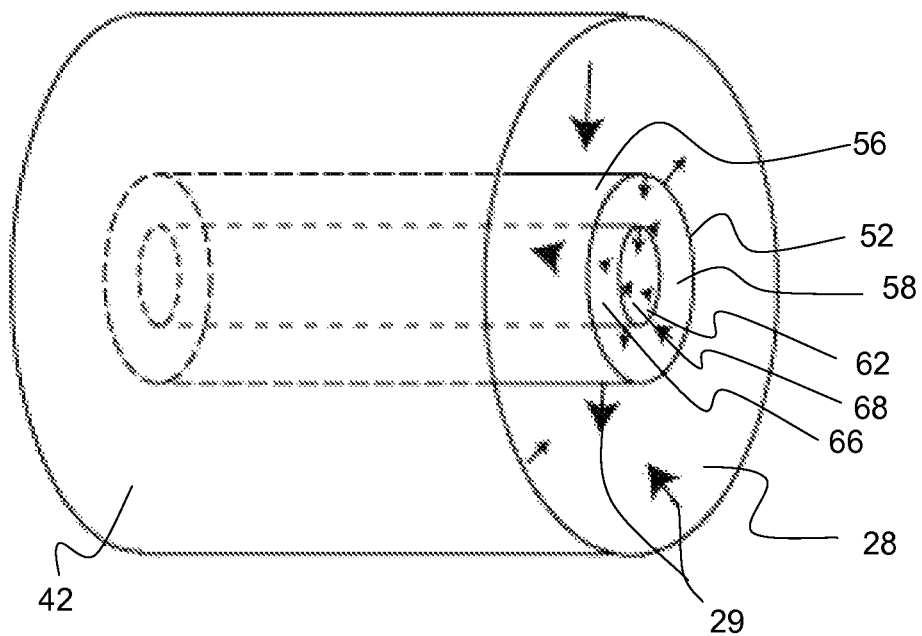
Figure 12:
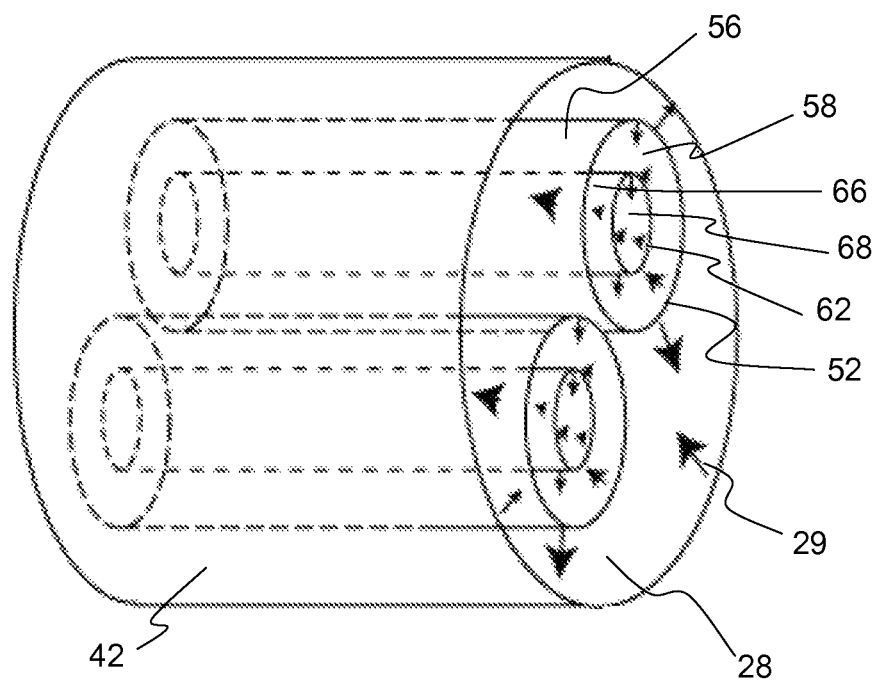

FIGS. 11 and 12 illustrate other exemplary ion source configuration in which a plurality of co-centric tubes (e.g., 52, 62) (forming a nested set of tubes) are employed in the ionization region. FIG. 12 illustrates provision of more than one nested set of tubes. The inner surface 28 of outer tube 42 and the inner (58, 68) and outer (56, 66) surfaces of the inner tubes (52, 62) are provided with radioisotopes and emit particles. The ionization region and the ion source elements are illustrated as cylindrical in shape. These elements are however not particularly limited in shape and their size is adjusted to the ionization volume desired and such that substantially all of the ionization region volume is exposed to emitted particles. Different radioisotopes may be provided on different surfaces.

In all of the embodiments of FIG. 5-12 it will be appreciated that the bars, rods or tube elements of the ion source may be discontinuous or continuous along the length of the ionization region. These elements can be made of any materials appropriate for the application as long as an electric field gradient can be established and maintained along the length of the ionizer It will be appreciated that combinations of the tubes and bars illustrated in FIGS. 5-12 can be made in a given ionization region if desired.

Figure 13:
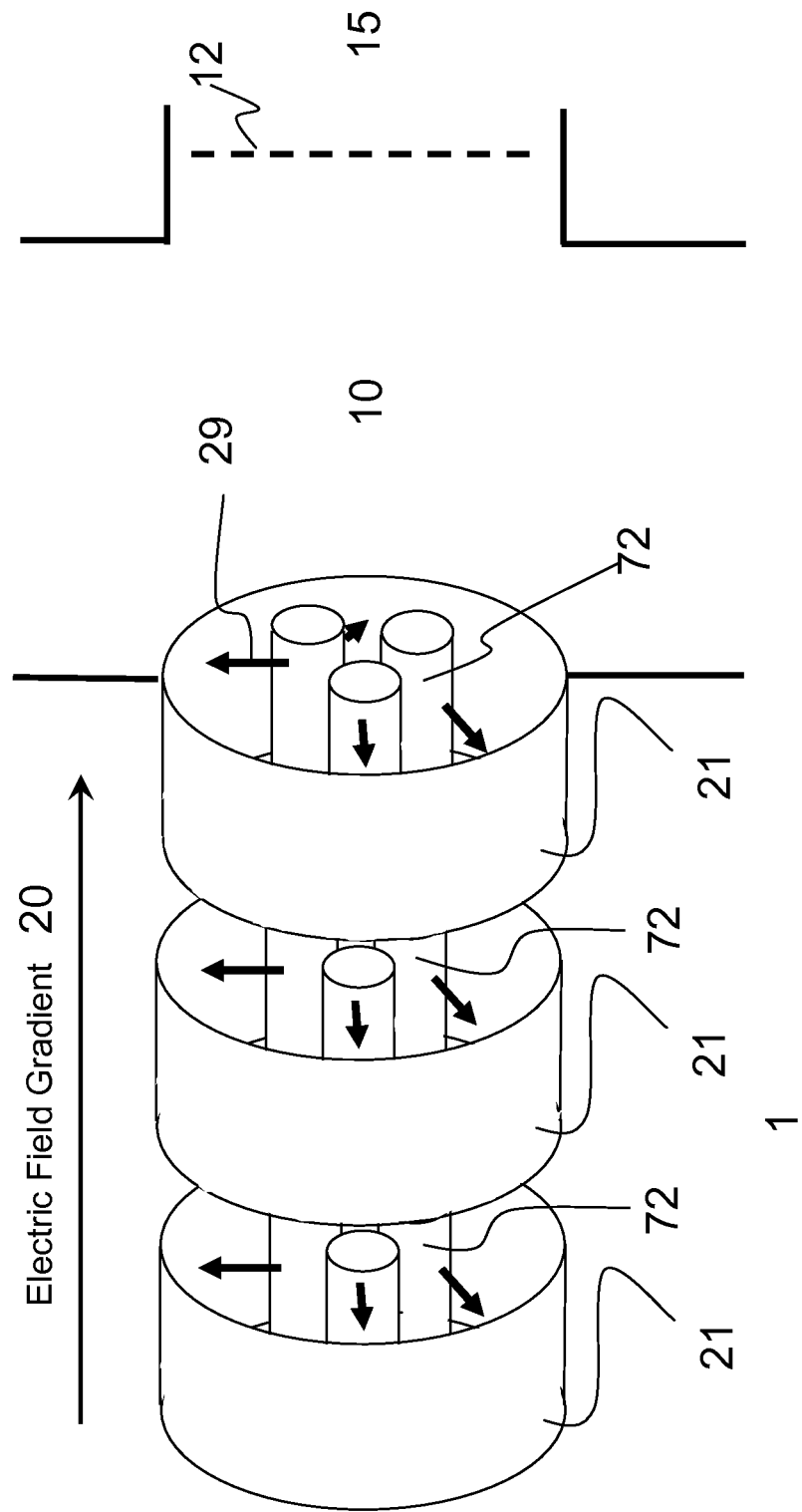
FIG. 13 is a schematic drawing illustrating an exemplary embodiment of a selected radioactive source configuration including ring electrodes for establishing a drift field in the ionization region. Any of the specific ion source configurations of FIG. 5-12 can be readily combined with a series of such ring electrodes. In these configurations the ion sources is configured into segments as shown in FIG. 13 for compatibility with the ring electrodes and the formation of the electric field gradient. The word "ring" is used to describe any electrode structure that will produce a controlled field gradient.

FIG. 13 illustrates an ionization region configuration in which ring electrodes 21 are provided. The word "ring" is used to describe any electrode structure that will produce a controlled field gradient. The use of a plurality of bars or tubes (42, 44, 52, etc.) which are discontinuous along the length of the ionization region is compatible with the formation of the electrical filed gradient by the ring electrodes. In the illustrated embodiment a plurality of ion source elements 72 carrying radioisotope and emitting particles (see arrows 29) are provided within the ring electrodes. The inner surface of the ring electrodes may also be provided with radioisotope and emit particles.

Each of the ionization regions illustrated in FIGS. 5-12 and 13 can be implemented in the system configurations of FIG. 2A, 3 or 4 and in the IMS instruments of FIGS. 2B-2D. It will be apparent to one of ordinary skill in the art that various support elements can be used to hold the ion source elements (bars and tubes) in a desired relative position with respect to each other and with respect to the inner wall(s) of the ionization region.

Figure 14:
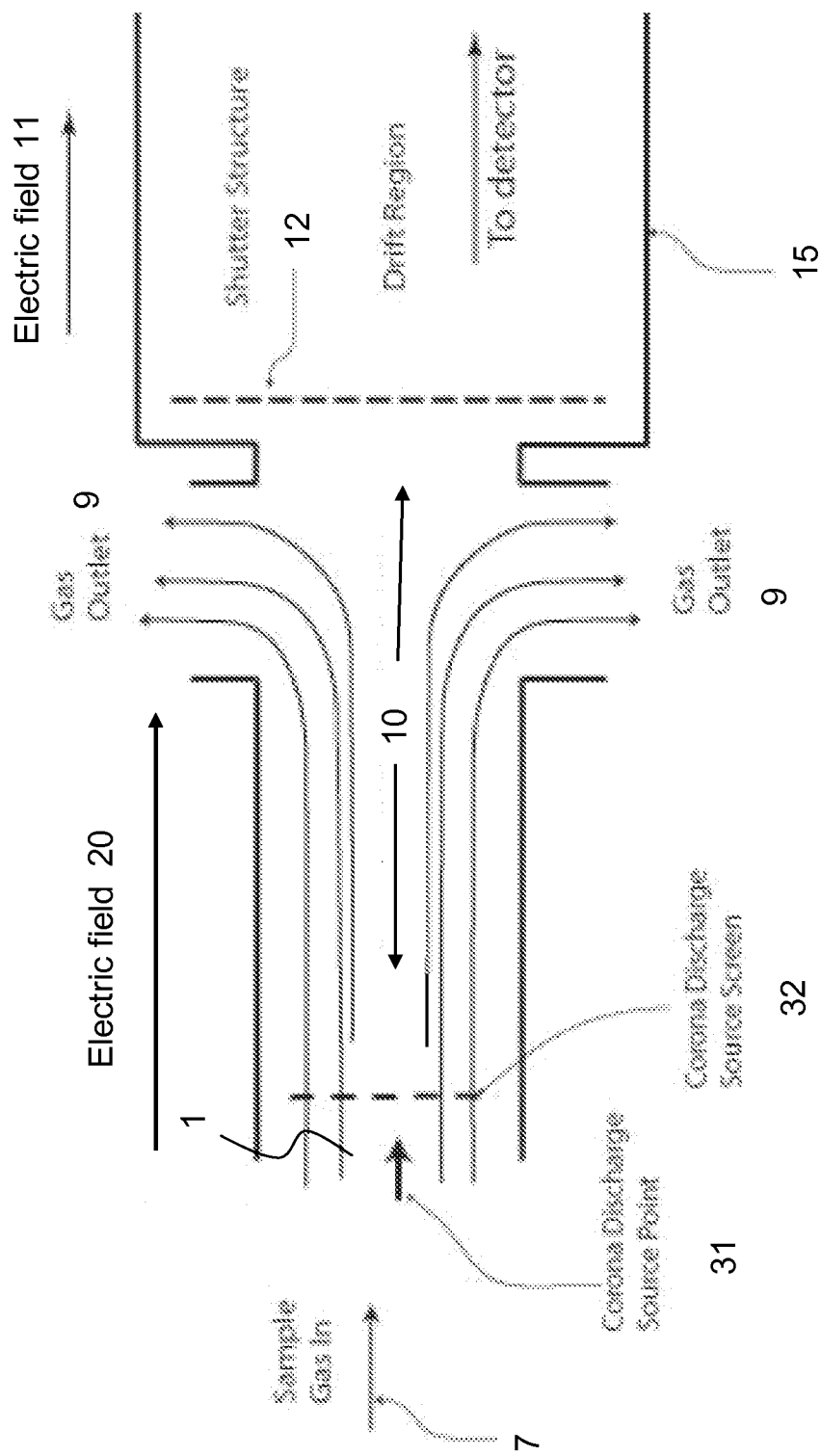
FIGS. 14-16 are schematic drawings illustrating exemplary embodiments of the systems of the invention including corona discharge ion sources.
Figure 15:
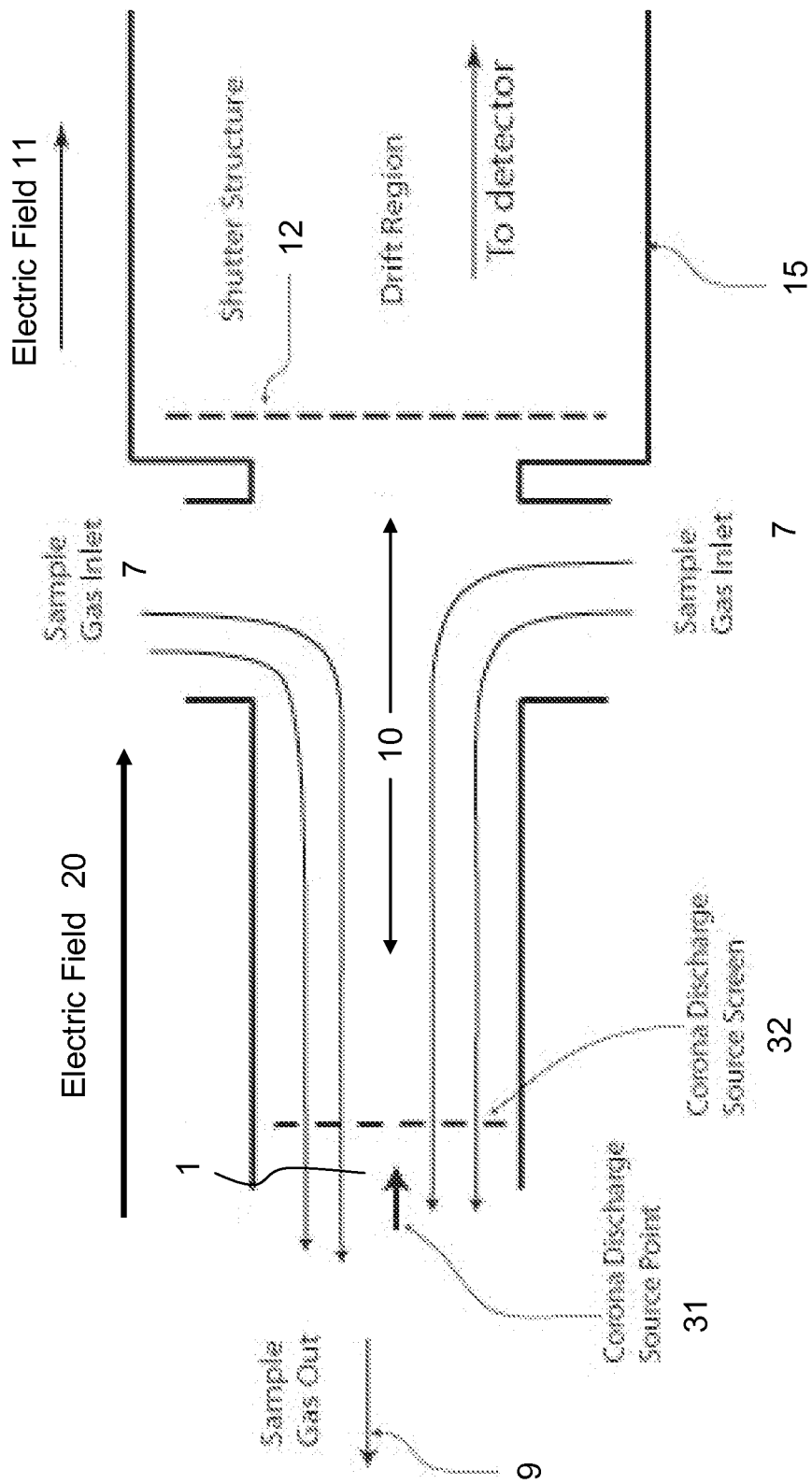
Figure 16:
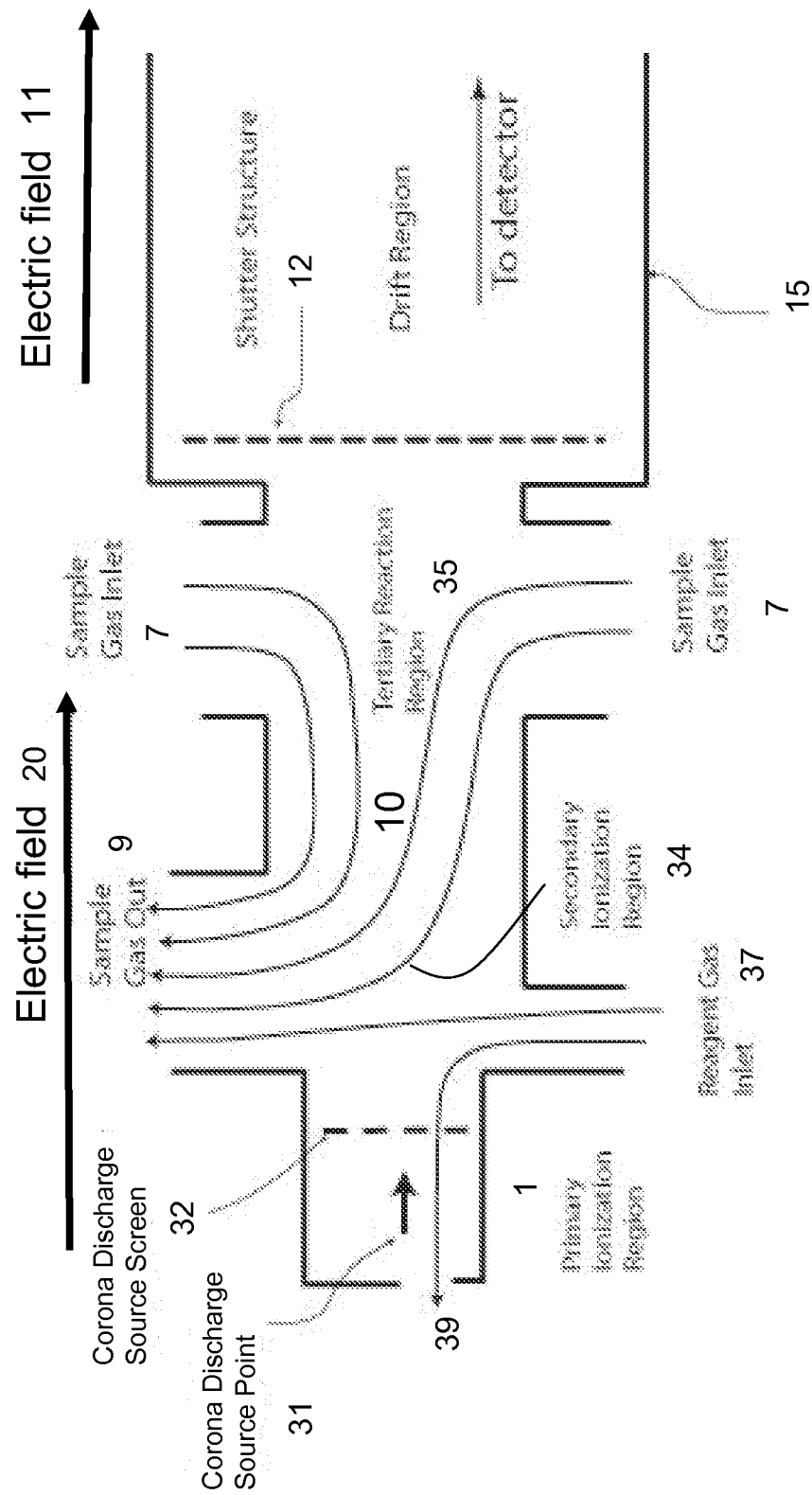

FIGS. 14-16 illustrate exemplary embodiments of the present invention in which one or more corona discharge sources is employed as the ionization source in the ionization region. A corona discharge source is schematically illustrated in these figures with a corona discharge point and a corona discharge screen. Any art-known corona discharge configuration useful as an ion source can be used in the instruments of this invention. See: Madani, M. R.; Miller, Toby A. "Current Density Distribution Measurement Of Negative Point-To-Plane Corona Discharge." IEEE Transactions on Instrumentation and Measurement (1998), 47(4), 907-913; Cross, J. A. "An Analysis Of The Current In A Point-To-Plane Corona Discharge And The Effect Of A Back-Ionizing Layer On The Plane." Journal of Physics D: Applied Physics (1985), 18(12), 2463-71. For example, more than one corona point electrode can e combined with a corona discharge screen to provide a multipoint corona discharge. See: Jaworek, A.; Krupa, A. "Electrical Characteristics Of A Corona Discharge Reactor Of Multipoint-To-Plane Geometry." Czechoslovak Journal of Physics (1995), 45(12), 1035-47.

FIG. 14 illustrates a corona discharge ion source in a configuration in which the sample gas is introduced into the system in the direction of ion electrophoresis. FIG. 15 illustrates a corona discharge ion source configuration in which the sample gas is introduced into the system in direction that is opposite to that of the direction of ion electrophoresis. FIG. 16 illustrates another corona discharge ion source configuration in which the sample gas does not directly contact the corona discharge. A reagent gas is introduced at inlet 37 and exits at outlet 39 or sample gas outlet 9. The sample gas is introduced downstream of the corona discharge and exits at sample gas outlet 9. The flow of reagent gas tends to prevent sample gas from contacting the corona. In this configuration, the majority of primary ions formed are those of the majority gases in the reagent gas stream, which may be air. The primary ions transfer charge to the reagent (secondary ions) and those in turn transfer charge to the sample (tertiary). The primary and secondary ions continue to move through the reaction region to form tertiary ions. Ions eventually enter the drift region after passage through the ion shutter.

In an embodiment of the present invention the need for preconcentration of certain analytes is removed, i.e., it is not necessary to either collect particles of analyte or to condense analytes from the vapor to the solid or liquid phase. Engineering benefits of the elimination of preconcentration include decreased analysis time and simplification of the instrument.

In spite of their inefficiencies, preconcentration techniques can result in an increase in sensitivity in IMS. It is an objective of the present invention to provide an embodiment in which an even more sensitive IMS instrument is achieved by combining preconcentration with the large-volume ionizer described herein.

In one embodiment of the invention, a large-surface area, preconcentrating sample collection device is connected to an IMS instrument incorporating a large-volume ionizer and large volume reaction region, and coupled to a suitable ion-shutter, drift-region, and detector. In this embodiment, analyte molecules from a very large volume, perhaps thousands of liters of very dilute vapor-phase analyte, perhaps at parts per quintillion or lower concentration, are allowed to adsorb onto a surface of hundreds of square centimeters, followed by desorption of the sample into a much smaller volume of gas, perhaps one liter, would provide a large increase in concentration of analyte vapor entering the IMS instrument. It is anticipated that combination of preconcentration with the increased sensitivity of the large-volume ionizer techniques described herein will result in a multiplicative effect on sensitivity, that is, even greater sensitivity.

In another embodiment, an IMS instrument incorporating large-volume ionizer features described herein would be connected to a membrane separation device that allows passage of analyte molecules and reduces the potential influence of external gasses.

In another embodiment of the invention, an IMS instrument incorporating large-volume ionizer features described herein would be connected to a sample separation device, such as a gas chromatograph, to provide for separation of molecular species prior to IMS analysis. This pre-separation allows quantitative analyses of analyte mixtures and semi-quantitative analyses of even more complex mixtures.

It should be apparent that there are many modifications possible with this invention, as long as the concept of using a large volume ionizer, relative to conventional practice, is followed. It is intended that the scope of the invention be defined by the appended claims.

Further, elements and/or features of different exemplary embodiments may be combined with each other and/or substituted for each other within the scope of this disclosure and appended claims.

In other embodiments, any one of the above-described and other exemplary features of the present invention can be embodied in the form of an apparatus, method, or system. For example, the aforementioned methods are embodied in the form of a system or device, including, but not limited to, any of the structures for performing the methodology illustrated in the drawings.

Any of the methods described are embodied in the form of a system or device, including, but not limited to, any of the structures for performing the methodology illustrated in the drawings. Any of the instruments, systems or devices described herein, particularly those in the drawings, can be embodied in a method employing the disclosed instruments, systems or devices.

Example embodiments being thus described, it will be clear to one of ordinary skill in the art that the same may be varied in many ways. Such exemplary variations are not to be regarded as a departure from the spirit and scope of the present invention, and all such modifications as would be obvious to one skilled in the art are intended to be included within the scope of the claims which follow.

The number of constituent elements, locations, shapes and so forth of the constituent elements are not limited to any of the structure for performing the methodology illustrated in the drawings.

When a group of materials, device components, configuration, or methods is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a distance range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. The term "comprising" is intended to be broader than the terms "consisting essentially of" and "consisting of", however, the term "comprising" as used herein in its broadest sense is intended to encompass the narrower terms "consisting essentially of" and "consisting of", thus the term "comprising" can be replaced with "consisting essentially of" to exclude steps that do not materially affect the basic and novel characteristics of the claims and "comprising" can be replaced with "consisting of" to exclude not recited claim elements.

The invention illustratively described herein suitably may be practiced in the absence of any element or elements, limitation or limitations which is not specifically disclosed herein.

One of ordinary skill in the art will appreciate that materials, device elements, device configurations and methods other than those specifically exemplified herein can be employed in the practice of the invention without resort to undue experimentation. All art-known functional equivalents, of any such materials, device elements and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art. For example, when a compound is claimed, it should be understood that compounds known in the art including the compounds disclosed in the references disclosed herein are not intended to be included in the claim.

All references cited herein are hereby incorporated by reference to the extent that there is no inconsistency with the disclosure of this specification. Some references provided herein are incorporated by reference to provide details concerning sources of starting materials, additional starting materials, additional reagents, additional methods of synthesis, additional methods of analysis and additional uses of the invention.

In the following discussion, the explosive TNT (trinitrotoluene, formula weight 227) will be used as an example trace vapor analyte with respect to the operation of an IMS such as that of FIG. 1 for its detection. In practice, the sample does not need to be TNT, nor does the carrier gas need to be air. This discussion can be generalized to other analyte vapors carried in other gasses.

Ions move in electrophoresis at a velocity proportional to the "reduced mobility" parameter unique to each ion species, and to the imposed electric field gradient. At atmospheric pressure and a field gradient of 200V/cm, this velocity ranges from 200 to 600 cm/s [check the max for Cl—, etc.]. For TNT, the ion velocity would be near 300 cm/s.

For improved resolution, an aperture grid 17 (see FIG. 1) serves as a guard for the collector plate 16 to prevent precharging of the collector due to charging by the approaching "ion packet." This grid also helps maintain the uniformity of the electric field responsible for the motion of the ions.

It is not necessary that the drift tube be round or any particular shape, but the parameters of the electrode array must allow a packet of ions released by the shutter (or pulsed ion source) to arrive at the collector plate electrode 16 (FIG. 1) with the minimum distortion in time, i.e., ideally, ions on the frontal boundary of a packet should arrive at 16 simultaneously. Similarly, it is not necessary that either the ionization region or the reaction region be round or any particular shape.

Periodically, the ion shutter 12 (a charged grid or grids) is opened to allow a pulse of ions into the drift chamber 15. The time of arrival of each ion species at the collector plate 16 is determined by the ion mobility in a non-ionizing gas filling the drift chamber 15. The quantity of ions collected as a function of drift time is recorded by a microprocessor (not shown).

Typically the ion shutter 12 is "opened" (or an ion source is pulsed) for a time range between 100 and 1000 µs to allow passage of an ion packet. The current measuring devices used in modern day IMSs are only able to measure currents in the picoamp range, or approximately 6 million ions per second. Multiplication by the width (typically 1000 µs of an ion packet arriving at the detector and using the approximation of the peak shape as a triangle reveals that each detectable packet contains approx 3000 ions. This would be the nominal detection limit for a commercial IMS containing a Ni-63 radioactive ionization source of approximately 10 mCuries radioactivity.

The response of the IMS device is proportional to both ionizer activity and sample size over large ranges. Miniature IMS devices might only contain 10 µCuries of radioactive material. As a result, a sample nominally 1000 times larger must be introduced to a miniature IMS device to produce an ion packet of 3000 ions, when compared with a stationary IMS device containing 10 mCuries of radioactive material. To reduce the sample size and thus the detection limit, it is desirable either a) to increase the sensitivity of the detector to available ions, b) increase the number of ions in a packet, or c) to cause the number of ions of a single analyte to arrive within a shorter time thus increasing the momentary ion current. All three circumstances increase the signal-to-noise ratio of a sample measurement. Typically, many packets are analyzed (many "scans") and the results averaged to improve the final signal-to-noise ratio.

Existing IMS instruments uniformly collect explosive samples by filtering air to collect particles of the explosive, or by rubbing "swipes" on surfaces to collect particulate samples, or by condensing sample vapors onto a surface. These procedures "preconcentrate" the sample, so when condensed phase of the sample is evaporated into the gas phase, the highest possible gas phase concentration of sample is introduced to the ionization chamber of the IMS. Using these methods, commercial IMS instruments achieve "tens of picograms" sensitivity to explosives.

The inventors are not aware of IMS instruments that can detect "tens of picograms" of any material without preconcentration. Furthermore, the sample is only analyzed using dried gas. In addition, it is often the case in this field that a "reagent" gas is employed to facilitate charge transfer to the analyte molecules.

The overall efficiency of commercial instruments can be calculated by reference to the 3000 ion detection limit. The packets of 3000 ions of the explosive TNT would weigh a total of 1.1 attogram ("ag") per scan. Assuming that 25 scans at a repetition rate of 25 scans per second are averaged to acquire the data, 27.5 ag of TNT ions pass through the shutter. If these ions came from 10 picograms of sample, then only 0.00028% of the introduced mass reached the detector. Accounting for the 0.1% duty cycle of the typical shutter gives an ionization efficiency of 0.28%. If the term "tens of picograms" really means 50 pg, the ionization efficiency is more probably 0.05%. The low efficiency of the preconcentration/evaporation method may be due, in part, to thermal decomposition of the sample during heating on the solid surface of the heater.

To maximize the concentration of sample for detection, the ionization chambers in commercial instruments are small—typified by a cylinder with internal radius equal to the penetration length in air of the beta particles emitted by the radioisotope Ni63, (approx 3 mm) and length of about 5 mm or a volume of 0.135 cm$^3$. Siegel states (M. W. Siegel, in T. W. Carr, Plasma Chromatography, Plenum Press, New York, 1984, pg 97ff) that the size of the chamber should be small to minimize loss of sample ions on the walls of the ionizer and to increase the linear flow velocity to minimize the time available for ion recombination. Siegel's analysis does not include the effect of an electrical field applied to the ionizer, and does not discuss ionizers with larger radii. The application of an electric field greatly minimizes ion recombination by rapidly separating positively and negatively charged particles.

The volume of air containing 10 pg of TNT can be estimated. The concentration of TNT in air at equilibrium ("saturation") between crystalline TNT solid and air at room temperature and pressure is $10^{-9}$ g TNT/g air. At room temperature and a density of 1.18 g/L, 8.49 cm$^3$ of air saturated with TNT would contain 10 pg of TNT. This volume is roughly 63 times that of the commercial IMS ionizer above.

Ambient air passing over a sample of TNT is not expected to be near the saturated concentration of TNT. Dilution of such an air stream by additional ambient air or other gas would further reduce the concentration. If the concentration of TNT reaching the IMS device is 1/100 or 1/10000 of saturation, 0.085 to 8.5 L of air must be introduced to the ionizer to ensure that 10 pg of TNT have been admitted.

If 25 scans at a repetition rate of 25 scans/s (a total sampling time of 1 s) were required to acquire a detection-limit sample of 10 pg, a flow rate of 85-8,500 cm$^3$/s (0.085-8.5 L/s) would be needed. Normally, the flow rate into the commercial ionizer described above is on the order of 100 cm$^3$/min or 1.7 cm$^3$/s. Clearly, the TNT present in ambient air cannot be detected using a conventional ionizer.

Ions only move "electrically downhill", i.e., negative ions (anions) only move toward regions of more positive voltages and positive ions (cations) only move toward regions of more negative voltages. The same phenomena occur in the ionizer when the ionization region is subjected to an electric field. Advantage can be taken of this to draw the ions out of the gas stream in the direction of the ion shutter and drift region. At an applied electric field gradient of 200 V/cm, TNT ions move under electrophoresis at 300 cm/s relative to the gas that carries them. After the carrier gas has passed through the ionizer, it must be removed through some sort of vent. To minimize the loss of ions to entrainment in gas moving out the vents, the air must only move slowly in the direction transverse to the ion flow as the air leaves the reaction region.

Carrier gas can flow through the ionization chamber either in the same direction as the analyte ions travel under electrophoresis toward the ion detector ("co-flow"), or in the opposite direction ("counter-flow"), or transverse to the ion flow ("cross-flow"). In an instrument using counter-flow, the linear velocity of the gas in the direction opposite to that of analyte ion electrophoresis must not exceed the velocity of the analyte electrophoresis, or the analyte ions will never reach the detector, but will be entrained and carried out through the vent. In instruments using co-flow and in instruments using cross-flow, excessive carrier gas flow will entrain some of the analyte ions and some fraction of the analyte ions will never reach the detector.

Both the counter-flow and cross-flow modes of operation may have at least the advantage that the sample molecules would not be exposed to reactive ions of the undesired charge sign. That exposure could lead to decomposition of sample molecules and to a loss of sensitivity.

An optimally designed ionizer for IMS instruments must allow gas flow at a rate compatible with the drift times and data processing times necessary in the rest of the instrument. Using a "plug-flow" model of gas flow in a cylinder, ionization of a disc-shaped volume of air containing sample must occur in the time between mixing of the neutral sample molecules with reactive ions and the time the ions reach the shutter. The majority of the gas must exit the instrument before it reaches the shutter, so the drift region is not disturbed, and the exiting gas can entrain and carry some sample molecules out of the reaction region if the samples molecules have not been ionized within the ionizer chamber. There will be some optimal linear flow velocity for every arrangement of ionizer region-, reaction region-, and ventilation region-geometries.

In an application where the ionization occurs by direct photoionization of sample molecules to directly create positively charged analyte ions, there is no need for a reaction region. Electrons freed by the photoionization move away from the detector, and it may be advantageous to utilize counter-flow to minimize exposure of the sample molecules to the electrons. Depending on the nature of the analyte molecules, there might be no deleterious reaction with electrons.

In an application where an electron source (plasma, corona discharge, photoemission, etc.) is used to produce negatively charged analyte ions, it is expected that few or no positively charged ions will be created. In this case, carrier flow could be either co-flow or counter-flow, with little difference in instrument sensitivity.

Numerical Example

An IMS analysis of TNT in the vapor phase will be illustrated. The analysis is based on the commercial 3000 electron/s detector electronics and the 1/10000 saturation factor described above.

Advantage may be taken of the relatively large penetration range (approx 5 cm) of the alpha particles emitted by the radioisotope Am241 (Americium-241). The entire cross-section of a cylindrical ionizer with a 4" (10.16 cm) inner diameter and length 4" would be exposed to alpha particles from an Am241 source located on the central axis of the cylinder. At an average linear velocity of 224 cm/s (5 mph), the 4" ID tube would pass $18.2 \times 10^3$ cm$^3$/s or double the required flow rate of 8,5000 cm$^3$/s (less if the concentration is greater). If the air were vented by a circumferential opening 2" long, the radial air velocity would be 10 cm/s, which is low enough to minimize loss of ions to entrainment.

The highest conversion of sample molecules to sample ions occurs when an excess number-density of reactive ions is generated relative to the number-density of sample molecules, and that the reactive ions are in contact with the sample molecules for a time period sufficient to convert the maximum of sample molecules to sample ions.

Siegel states than the generation rate of ions within an ionizer is $10^6 \times$(activity in milliCuries)$\times$(particle energy in eV)/volume. In the Experimental Example below, using 2.7 mCi of Am241 (particle energy 4.5 MeV) in a 4" diameter$\times$4" ionizer, this is $9.88 \times 10^9$ charges/cm$^3$/s. Siegel also states that the second order reaction rate constant for charge exchange between analyte and reactive ions is $10^{-9}$ cm$^3$ s$^{-1}$. The time required for analyte to be 90% ionized is thus 0.01 second. This is shorter than with the residence time (0.045 s) of air in the 4" ID$\times$4" cylindrical ionizer at 5 mph linear flow, and shorter than the time (0.051 s) of a singly charged TNT ion to traverse the 4" ionizer and a 2" reaction region at 200V/cm (ignoring the air flow). As a result, nearly complete ionization of the TNT sample vapor is expected.

These comparisons suggest that the linear velocity of gas flow in the spectrometer and the length of the ionizer/reaction region are interdependent. Effective ionization will occur at large volumetric flow rates, if the reaction region is long enough for charge transfer between reactive ions and analyte molecules to be essentially complete.

Alternatively, an apparatus containing multiple radioactive sources of smaller penetration range, for instance the beta particle emitting isotope Ni63, with a penetration depth of 3 mm, could be used to expose a large diameter stream, or multiple streams of sample-containing gas to ionizing radiation. As another alternative, a light source could be used to photoionize sample molecules contained in a gas, perhaps with reflecting mirrors to allow increase exposure of the sample to photons. As yet another alternative, an electron source of several possible types could be used in place of a radioisotope source.

The radioactive material could be on the inner surface of the ionization chamber, allowing the energetic particles to radiate inward toward the axis of the chamber. Preferably, the radioactive source could be located on or near the inner axis of the chamber so emitted particles radiate outward. This geometry is potentially more efficient at generating reactive ions for a given radioactivity level, because all particles will create reactive ions until they have lost all their kinetic energy. To maximize efficiency in an ionizer where the radioactive material is on the inner surface of the chamber and the particles radiate inward, care must be taken to avoid having any chamber wall within the penetration range of the particles. Particles that strike the wall of the ionizer or any solid material are lost before they have generated the maximum number of reactive ions.

The conventional data acquisition/processing rate is 10-50 scans/s. At the example rate of $18.2\times10^3$ $cm^3/s$, the 4" ID×4" long ionizer will be completely refilled 15 times per second. This replenishment rate would assure that, at acquisition rates of 15 scans/s, fresh sample vapor would be available for every scan.

It is possible to increase the electrophoretic velocity of ions in the reaction region to reduce the influences of the flow of carrier gas, but there is a limit to the allowable electric field gradient before ions enter the "high voltage regime" where ions are heated by collisions with gas molecules and unusual and/or unexpected chemical reactions occur. The transition to the high voltage regime occurs below 2000 V/cm for small molecules at atmospheric pressure.

Experimental Example

An ion mobility spectrometer (IMS) was built as a linear device with cylindrical symmetry along a central axis. All components were assembled perpendicular to—and centered on—the instrument axis. All components were aligned socket and tenon joints and were held in place by longitudinal ceramic rods and spring tension.

Sample flowed into the instrument first through a finned aluminum gas-heater provided with electric cartridge heaters and held with temperature control at 100 C, then flowed into the ionizer.

The ionizer was a 4 inch inner diameter (ID)×4" long ionization chamber consisting of four electrode rings ("drift rings") sealed and insulated by 4" ID ceramic rings. The ionizer was terminated at the sample entrance end by a perforated metal plate electrically attached to the first drift ring. Mounted on the central axis of the chamber was a metal foil charged with 2.7 mCi of Am241, protected by a gold film. Alpha particles from the foil radiated outward from the source foil into the sample gas.

After flowing through the ionization chamber, sample gas proceeded through a reaction region 2.5" long consisting of additional 4" ID metal drift rings separated by ceramic spacers. The sample gas containing predominantly neutral species was free to escape the region at low velocity through gaps between the drift rings (totaling an area of 162 $cm^2$).

Ions were passed by electrophoresis along the axis of the spectrometer to an ion shutter consisting of thin nickel screens, each with a 2" diameter area crosshatched by fine electroformed conductors. This shutter structure is described in U.S. published application 2008/0179515A1 (Jul. 31, 2008) (U.S. Ser. No. 11/769,513, filed Jul. 27, 2007).

The ion separation or "drift region" consisted of 11 additional metal drift rings sealed and insulated by ceramic rings, with a total length of 6". The drift tube was terminated by a thin nickel screen ("aperture grid") with a 2" diameter area crosshatched by fine electroformed conductors. The separated ions passed through the aperture grid and were neutralized at a 1" diameter Faraday plate electrode 1 mm from the aperture grid. The ion current formed at the Faraday electrode was amplified with a precision switched integrator detector similar to, but more sensitive than, a Texas Instruments IVC102 integrated circuit. Data was analyzed using a personal computer with attached data acquisition hardware and custom developed software.

A potential difference of approximately −5000 volts was applied across the ionizer and reaction region, and approximately −7000 volts across the drift region between the shutter and the Faraday electrode. The potential between the aperture grid and the Faraday plate was −200 volts; this gradient should have collected the majority of the ions with a small loss in peak resolution.

Hot air that passed through the vents in the reaction region was used to heat the outside of the drift region. The air was removed from the IMS with a 4" ID duct hose through a calibrated 4" anemometer and a speed controlled fan. The exit air temperature was 97 C, and the measured air velocity was variously 4 to 5 MPH.

Twenty milliliters of acetonitrile containing 0.2 grams of dissolved trinitrotoluene (TNT) were evaporated overnight at room temperature in the bottom of a 9"W×13"L×1.5"D glass tray. This tray was placed in a little-used building corridor 12 feet high and 8 feet wide, with an average air velocity of approximately ⅓ foot per second, as determined by watching puffs of smoke. The mass flow of air was thus 1.07 kgm/s. The evaporation rate of TNT vapor from solid TNT is known to be approximately 26 $pg/cm^2/s$, so the concentration of TNT in air was approximately 5 ppt. (Mu, R.; Ueda, A.; Liu, Y. C.; Wu, M.; Henderson, D. O.; Lareau, R. T.; Chamberlain, R. T. "Effects of interfacial interaction potential on the sublimation rates of TNT films on a silica surface examined by QCM and AFM techniques." Surface Science (2003), 530(1-2), L293-L296.)

TNT was observed in the IMS spectrum as a single peak approximately 6 times as high as the estimated baseline noise when the glass sample tray was place 71 feet upwind of the IMS instrument, at a time corresponding to the drift velocity of the air in the corridor (3.5 minutes). The peak decreased to zero height within 10 minutes when the tray was removed. Larger peaks were observed when the tray was introduced closer to the instrument, and when the tray was very close, it was necessary to place it directly upstream from the IMS, so the vapors did not bypass the instrument. The IMS drift time for TNT was confirmed with commercial analytical TNT solution applied to a glass ticket heated directly in front of the IMS instrument. Each analytical IMS spectrum was the average of 200 scans and required approximately 15 seconds to complete, including data acquisition, analysis, and presentation on a personal computer. Prior to introduction of the sample to the corridor, a background spectrum was collected in the same way. This spectrum was subtracted from each subsequent analyte spectrum. In a separate experiment, using the same glass tray with 800 mg of TNT and the same IMS, this level of TNT could be detected at a distance of 135 feet from the tray.

The temperature and relative humidity in the corridor at the time of the experiment were 85 F and 62% RH. No reagents were added to either the TNT sample or the air stream at any point, and no attempt was made to dry the air stream at any point.

We claim:

1. An ion mobility spectrometer for detection of analyte which comprises:
    a sample inlet for continuously receiving a flow of sample gas wherein the volumetric flow of sample gas is greater than 85 $cm^3/s$;
    an ionization region for formation of primary ions which comprises an ion source, wherein the ionization volume of the ionization source is greater than 5 $cm^3$;
    a reaction region for receiving the flow of sample gas and primary ions,
    wherein primary ions charge transfer to generate secondary and tertiary ions including analyte ions;
    an ion shutter;
    a drift region having an electric field gradient; and
    an ion detector;
    wherein the ion shutter gates the entrance of ions into the drift region, the ions in the drift region drift in the electric field gradient in the direction of electrophoresis at the velocity of ion electrophoresis to be detected at the ion detector, thereby allowing detection of analyte, and
    wherein the linear flow velocity of sample gas in the direction perpendicular to the direction of ion electrophoresis is less than 20% of the velocity [of the velocity] of ion electrophoresis.

2. The ion mobility spectrometer of claim 1 wherein the flow of sample gas is not dried.

3. The ion mobility spectrometer of claim 1 wherein the direction of flow of the sample gas is transverse to or opposite in direction to the direction of electrophoresis.

4. The ion mobility spectrometer of claim 3 wherein the ionization volume of the ionization source is between 0.5 L and 2 L.

5. The ion mobility spectrometer of claim 3 further comprising an electric field gradient in the ionization region.

6. The ion mobility spectrometer of claim 3 wherein the ion source is one or more radioactive ionization sources.

7. The ion mobility spectrometer of claim 3 wherein the flow of sample gas is not dried.

8. The ion mobility spectrometer of claim 1 wherein the direction of flow of the sample gas is opposite in direction to the direction of electrophoresis.

9. The ion mobility spectrometer of claim 1 wherein the ion source is one or more radioactive ionization sources.

10. The ion mobility spectrometer of claim 1 wherein the ion source is a corona discharge or a photoionization source.

11. A method for detecting analyte in a sample gas by ion mobility spectroscopy which comprises the steps of:
    (a) providing an ion mobility spectrometer (IMS) having a sample inlet for continuously receiving sample gas, an ionization region for formation of primary ions which comprises an ion source, wherein the ionization volume of the ionization source is greater than 5 $cm^3$; a reaction region for receiving the flow of sample gas wherein primary ions charge transfer with analyte to generate secondary and tertiary ions; an ion shutter; a drift region having an electric field gradient providing a direction of electrophoresis of ions and an ion electrophoresis velocity in the direction of electrophoresis therein; and an ion detector;
    (b) continuously introducing sample gas to be assessed for the presence of analyte into the ionization region of the IMS and forming primary ions, such that volumetric flow of sample gas is greater than 85 $cm^3/s$ and the linear velocity of the sample gas in a direction perpendicular to the direction of ion electrophoresis is less than 20% of the velocity of the ion electrophoresis and forming primary ions;
    (c) forming secondary and tertiary ions, including any analyte ions, in the reaction region; and
    (d) detecting the ions formed in the IMS, to thereby detect the presence of analyte.

12. The method of claim 11 wherein the flow of sample gas is not dried.

13. The method of claim 11 further comprising a step of preconcentration of the sample.

14. The method of claim 11 wherein the sample gas is ambient air.

15. The method of claim 11 wherein the volumetric flow rate of sample gas is 85-/s 8,500 $cm^3/s$.

16. The method of claim 11 wherein the direction of flow of the sample gas is transverse to the direction of electrophoresis.

17. The method of claim 11 wherein the direction of flow of the sample gas is opposite in direction to the direction of electrophoresis.

18. The ion mobility spectrometer of claim 1 wherein the flow of sample gas does not enter the drift region.

19. The method of claim 11 wherein the flow of sample gas does not enter the drift region.

* * * * *

UNITED STATES PATENT AND TRADEMARK OFFICE
CERTIFICATE OF CORRECTION

PATENT NO.        : 9,134,272 B2
APPLICATION NO.   : 14/046447
DATED             : September 15, 2015
INVENTOR(S)       : M. Bonner Denton and Roger P. Sperline Page 1 of 1

It is certified that error appears in the above-identified patent and that said Letters Patent is hereby corrected as shown below:

In the Claims:

In column 9, claim 1, line 41, delete "[of the velocity]".

In column 20, claim 15, line 43, delete "/s". (First Occurrence)

Signed and Sealed this
Twenty-fourth Day of May, 2016

Michelle K. Lee
*Director of the United States Patent and Trademark Office*